United States Patent [19]
Oppermann et al.

[11] Patent Number: 5,614,385
[45] Date of Patent: Mar. 25, 1997

[54] METHODS AND COMPOSITIONS FOR HIGH PROTEIN PRODUCTION FROM RECOMBINANT DNA

[75] Inventors: Hermann Oppermann, Medway; Haimanti Dorai, Lexington; Paul Kaplan, Auburndale, all of Mass.

[73] Assignee: Creative Biomolecules, Inc., Hopkinton, Mass.

[21] Appl. No.: 461,666

[22] Filed: Jun. 5, 1995

Related U.S. Application Data

[62] Division of Ser. No. 143,497, Oct. 25, 1993.

[51] Int. Cl.$^6$ .................................................. C12P 21/02
[52] U.S. Cl. ..................... 435/69.4; 435/254.2; 435/325
[58] Field of Search .................................. 435/69.1, 69.4, 435/70.1, 70.3, 240.2, 254.2

[56]  References Cited

U.S. PATENT DOCUMENTS

| | | | |
|---|---|---|---|
| 4,656,134 | 4/1987 | Ringold | 435/91.1 |
| 4,740,461 | 4/1988 | Kaufman | 435/69.1 |
| 4,956,288 | 9/1990 | Barsoum | 435/172.3 |
| 5,002,874 | 3/1991 | Kaufman | 435/69.1 |
| 5,024,939 | 6/1991 | Gorman | 435/69.1 |
| 5,238,820 | 8/1993 | Kaufman | 435/69.1 |
| 5,258,287 | 11/1993 | Baxter et al. | 435/69.1 |
| 5,354,557 | 10/1994 | Oppermann et al. | 424/423 |

FOREIGN PATENT DOCUMENTS

| | | |
|---|---|---|
| 0309237 | 9/1988 | European Pat. Off. . |
| 0378382 | 7/1990 | European Pat. Off. . |
| WO87/02707 | 5/1987 | WIPO . |
| WO-91A-05062 | 4/1991 | WIPO . |
| WO86/06409 | 11/1996 | WIPO . |

OTHER PUBLICATIONS

Perides et al. (1994), "Regulation of Neural Cell Adhesion Molecule and L1 by the Transforming Growth Factor-β Superfamily," 269 *J. Biol. Chem.* 1:765–770.

ten Dijke et al. (1994), "Identification of Type I Receptors For Osteogenic Protein–1 and Bone Morphogenetic Protein–4," 269 *J. Biol. Chem.* 25:16985–16988.

Rosen et al. (1992), "The BMP Proteins In Bone Formation and Repair," 8 *Trends In Genetics* 3:97–102.

Datta et al. (1991), "A Purified Adenovirus 289–Amino–Acid E1A Protein Activates RNA Polymerase III Transcription In Vitro and Alters Transcription Factor TFIIIC," 65 *J. Virology* 10:5297–5304.

Cockett, et al. (1991), "The Use of Engineered E1A Genes to Transactivate The hCMV–MIE Promoter In Permanent CHO Cell Lines," *Nucleic Acids Res.* 19:319–325.

Cockett, et al. (1990) "High Level Expression of Tissue Inhibitor Of Metalloproteinases In Chinese Hamster Ovary Cells Using Glutamine Synthetase Gene Amplification," *Biotechnology* 8:662–667.

Grinnell et al. (1987), "Transactivated Expression of Fully Gamma–Carboxylated Recombinant Human Protein C, An Antithrombotic Factor," *Biotechnology* 5:1189–1192.

West et al. (1987), "Gene Expression in Adeno–Associated Virus Vectors: The Effects of Chimeric mRNA Structure, Helper Virus, and Adenovirus $VA_1$RNA," 160 *Virology* 38–47.

Tibbetts et al. (1986), "Autoregulation of Adenovirus E1A Gene Expression," 57 *J. Virology* 3:1055–1064.

Foecking, et al. (1986) "Powerful and Versatile Enhancer–Promoter Unit For Mammalian Expression Vectors," *Gene* 45:101–105.

Wong et al. (1985), "Human GM–CSF: Molecular Cloning of Complementary DNA and Purification of the Natural and Recombinant Proteins," 228 *Science* 17:810–815.

*Primary Examiner*—James S. Ketter
*Attorney, Agent, or Firm*—Testa, Hurwitz & Thibeault, LLP

[57] ABSTRACT

Disclosed herein are improved methods and compositions for achieving enhanced protein production expressed from non-native gene constructs, including single chain sFv and derivative sequences. The methods and compositions are particularly useful for creating stably transfected, contitutively expressing immortalized mammalian cell lines that exhibit high recombinant protein productivity while maintaining a low copy number per cell of the non-native recombinant DNA sequence encoding the protein of interest.

30 Claims, 10 Drawing Sheets

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 1356 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..1356
        ( C ) OTHER INFORMATION: /note= "adcE1A"

( x i ) SEQUENCE DESCRIPTION: SEQ ID NO: 1:

```
CTGCAGGTCC  TGCTTCATCC  CCGTGGCCCG  TTGCTCGCGT  TTGCTGGCGG  TGTCCCCGGA    60

AGAAATATAT  TTGCATGTCT  TTAGTTCTAT  GATGACACAA  ACCCCGCCCA  GCGTCTTGTC   120

ATTGGCGAAT  TCGAACACGC  AGATGCAGTC  GGGGCGGCGC  GGTCCCAGGT  CCACTTCGCA   180

TATTAAGGTG  ACGCGTGTGG  CCTCGAACAC  CGAGCGACCC  TGCAGCGACC  CGCTTAACAG   240

CGTCCCTCCA  TGAGACATAT  TATCTGCCAC  GGAGGTGTTA  TTACCGAAGA  AATGGCCGCC   300

AGTCTTTTGG  ACCAGCTGAT  CGAAGAGGTA  CTGGCTGATA  ATCTTCCACC  TCCTAGCCAT   360

TTTGAACCAC  CTACCCTTCA  CGAACTGTAT  GATTTAGACG  TGACGGCCCC  CGAAGATCCC   420

AACGAGGAGG  CGGTTTCGCA  GATTTTTCCC  GAGTCTGTAA  TGTTGGCGGT  GCAGGAAGGG   480

ATTGACTTAT  TCACTTTTCC  GCCGGCGCCC  GGTTCTCCGG  AGCCGCCTCA  CCTTTCCCGG   540

CAGCCCGAGC  AGCCGGAGCA  GAGAGCCTTG  GGTCCGGTTT  CTATGCCAAA  CCTTGTGCCG   600

GAGGTGATCG  ATCTTACCTG  CCACGAGGCT  GGCTTTCCAC  CCAGTGACGA  CGAGGATGAA   660
```

| | | | | | | |
|---|---|---|---|---|---|---|
| GAGGGTGAGG | AGTTTGTGTT | AGATTATGTG | GAGCACCCCG | GGCACGGTTG | CAGGTCTTGT | 720 |
| CATTATCACC | GGAGGAATAC | GGGGGACCCA | GATATTATGT | GTTCGCTTTG | CTATATGAGG | 780 |
| ACCTGTGGCA | TGTTTGTCTA | CAGTAAGTGA | AAATTATGGG | CAGTCGGTGA | TAGAGTGGTG | 840 |
| GGTTTGGTGT | GGTAATTTTT | TTTTAATTTT | TACAGTTTTG | TGGTTTAAAG | AATTTTGTAT | 900 |
| TGTGATTTTT | TAAAAGGTCC | TGTGTCTGAA | CCTGAGCCTG | AGCCCGAGCC | AGAACCGGAG | 960 |
| CCTGCAAGAC | CTACCCGGCG | TCCTAAATTG | GTGCCTGCTA | TCCTGAGACG | CCCGACATCA | 1020 |
| CCTGTGTCTA | GAGAATGCAA | TAGTAGTACG | GATAGCTGTG | ACTCCGGTCC | TTCTAACACA | 1080 |
| CCTCCTGAGA | TACACCCGGT | GGTCCCGCTG | TGCCCCATTA | AACCAGTTGC | CGTGAGAGTT | 1140 |
| GGTGGGCGTC | GCCAGGCTGT | GGAATGTATC | GAGGACTTGC | TTAACGAGTC | TGGGCAACCT | 1200 |
| TTGGACTTGA | GCTGTAAACG | CCCCAGGCCA | TAAGGTGTAA | ACCTGTGATT | GCGTGTGTGG | 1260 |
| TTAACGCCTT | TGTTTGCTGA | ATGAGTTGAT | GTAAGTTTAA | TAAAGGGTGA | GATAATGTTT | 1320 |
| AACTTGCATG | GCGTGTTAAA | TGGGGCGGGG | AGATCT | | | 1356 |

( 2 ) INFORMATION FOR SEQ ID NO: 2:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..36
        ( C ) OTHER INFORMATION: /note= "E1Aprim1"

( x i ) SEQUENCE DESCRIPTION: SEQ ID NO: 2:

| | | | | |
|---|---|---|---|---|
| AAAGGCCTCC | ATGAGACATA | TTATCTGCCA | CGGAGG | 36 |

( 2 ) INFORMATION FOR SEQ ID NO: 3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..28
        ( C ) OTHER INFORMATION: /note= "E1Aprim2"

( x i ) SEQUENCE DESCRIPTION: SEQ ID NO: 3:

| | | | |
|---|---|---|---|
| AAAGATCTCC | CCATTTAACA | CGCCATGC | 28 |

( 2 ) INFORMATION FOR SEQ ID NO: 4:

( i ) SEQUENCE CHARACTERISTICS:
        ( A ) LENGTH: 2037 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..2037
        ( C ) OTHER INFORMATION: /note= "adeVA1"

( x i ) SEQUENCE DESCRIPTION: SEQ ID NO: 4:

| | | | | | | |
|---|---|---|---|---|---|---|
| AAGCTTGATC | TGCACCCTTG | GGTGTCGCTC | AGGAGAGGGC | GCTCCTAGCC | GCGCCAGGCC | 60 |
| CTCGCCCTCC | TCCAAGTCCA | GGTAGTGCCG | GGCCCGGCGC | CGCGGGGGTT | CGTAATCACC | 120 |
| ATCTGCCGCC | GCGTCAGCCG | CGGATGTTGC | CCCTCCTGAC | GCGGTAGGAG | AAGGGGAGGG | 180 |
| TGCCCTGCAT | GTCTGCCGCT | GCTCTTGCTC | TTGCCGCTGC | TGAGGAGGGG | GGCGCATCTG | 240 |
| CCGCAGCACC | GGATGCATCT | GGGAAAAGCA | AAAAGGGGC | TCGTCCCTGT | TTCCGGAGGA | 300 |
| ATTTGCAAGC | GGGGTCTTGC | ATGACGGGGA | GGCAAACCCC | CGTTCGCCGC | AGTCCGGCCG | 360 |
| GCCCGAGACT | CGAACCGGGG | GTCCTGCGAC | TCAACCCTTG | GAAAATAACC | CTCCGGCTAC | 420 |
| AGGGAGCGAG | CCACTTAATG | CTTTCGCTTT | CCAGCCTAAC | CGCTTACGCC | GCGCGCGGCC | 480 |
| AGTGGCCAAA | AAAGCTAGCG | CAGCAGCCGC | CGCGCCTGGA | AGGAAGCCAA | AAGGAGCGCT | 540 |
| CCCCCGTTGT | CTGACGTCGC | ACACCTGGGT | TCGACACGCG | GGCGGTAACC | GCATGGATCA | 600 |
| CGGCGGACGG | CCGGATCCGG | GGTTCGAACC | CCGGTCGTCC | GCCATGATAC | CCTTGCGAAT | 660 |
| TTATCCACCA | GACCACGGAA | GAGTGCCCGC | TTACAGGCTC | TCCTTTTGCA | CGGTCTAGAG | 720 |
| CGTCAACGAC | TGCGCACGCC | TCACCGGCCA | GAGCGTCCCG | ACCATGGAGC | ACTTTTTGCC | 780 |
| GCTGCGCAAC | ATCTGGAACC | GCGTCCGCGA | CTTTCCGCGC | GCCTCCACCA | CCGCCGCCGG | 840 |
| CATCACCTGG | ATGTCCAGGT | ACATCTACGG | ATATCATCGC | CTTATGTTGG | AAGACCTCGC | 900 |
| CCCCGGAGCC | CCGGCCACCC | TACGCTGGCC | CCTCTACCGC | CAGCCGCCGC | CGCACTTTTT | 960 |
| GGTGGGATAT | CAGTACCTGG | TGCGGACTTG | CAACGACTAC | GTCTTTGACT | CAAGGGCTTA | 1020 |
| CTCGCGTCTC | AGGTACACCG | AGCTCTCGCA | GCCGGGTCAC | CAGACCGTTA | ACTGGTCGTT | 1080 |
| ATGGCCAACT | GCAGCCCGGG | GGATCCACTA | GAAGAAGCTT | GGGATCCGGC | TGTGGAATGT | 1140 |
| GTGTCAGTTA | GGGTGTGGAA | AGTCCCCAGG | CTCCCCAGCA | GGCAGAAGTA | TGCAAAGCAT | 1200 |
| GCATCTCAAC | CAGACAGCAA | CCATAGTCCC | TCCCTAACT | CCGCCCATCC | CGCCCCTAAC | 1260 |
| TCCGCCCAGT | TCCGCCCATT | CTCCGCCCCA | TGGCTGACTA | ATTTTTTTA | TTTATGCAGA | 1320 |
| GGCCGAGGCC | GCCTCGGCCT | CTGAGCTATT | CCAGAAGTAG | TGAGGAGGCT | TTTTTGGAGG | 1380 |
| CTGCCATCAT | GGTTCGACCA | TTGAACTGCA | TCGTCGCCGT | GTCCAAAAT | ATGGGGATTG | 1440 |
| GCAAGAACGG | AGACCTACCC | TGGCCTCCGC | TCAGGAACGA | GTTCAAGTAC | TTCCAAAGAA | 1500 |
| TGACCACAAC | CTCTTCAGTG | GAAGGTAAAC | AGAATCTGGT | GATTATGGGT | AGGAAAACCT | 1560 |
| GGTTCTCCAT | TCCTGAGAAG | AATCGACCTT | TAAAGGACAG | AATTAATATA | GTTCTCAGTA | 1620 |
| GAGAACTCAA | AGAACCACCA | CGAGGAGCTC | ATTTCTTGC | CAAAAGTTTG | GATGATGCCT | 1680 |
| TAAGACTTAT | TGAACAACCG | GAATTGGCAA | GTAAAGTAGA | CATGGTTTGG | ATAGTCGGAG | 1740 |
| GCAGTTCTGT | TTACCAGGAA | GCCATGAATC | AACCAGGCCA | CCTCAGACTC | TTTGTGACAA | 1800 |
| GGATCATGCA | GGAATTTGAA | AGTGACACGT | TTTTCCCAGA | AATTGATTTG | GGGAAATATA | 1860 |
| AACTTCTCCC | AGAATACCCA | GGCGTCCTCT | CTGAGGTCCA | GGAGGAAAAA | GGCATCAAGT | 1920 |
| CTAAGTTTGA | AGTCTACGAG | AAGAAAGACT | AACAGGAAGA | TGCTTTCAAG | TTCTCTGCTC | 1980 |
| CCCTCCTAAA | GCTATGCATT | TTTATAAGAC | CATGGGACTT | TGCTGGCTT | TAGATCT | 2037 |

( 2 ) INFORMATION FOR SEQ ID NO: 5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA (ix) FEATURE:
    (A) NAME/KEY: misc_feature
    (B) LOCATION: 1..22
    (C) OTHER INFORMATION: /note= "VA1prim1"

(xi) SEQUENCE DESCRIPTION: SEQ ID NO: 5:

CCGACTGCAG TTGGCCATAA CG                                  22

(2) INFORMATION FOR SEQ ID NO: 6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..23
        (C) OTHER INFORMATION: /note= "VA1prim2"

(xi) SEQUENCE DESCRIPTION: SEQ ID NO: 6:

GGCACGCTTC AGCTGCACCC TTG                                23

METHODS AND COMPOSITIONS FOR HIGH PROTEIN PRODUCTION FROM RECOMBINANT DNA

This is a divisional of copending application Ser. No. 08/143,497 filed on Oct. 25, 1993.

FIELD OF THE INVENTION

The application relates generally to the field of recombinant gene expression.

BACKGROUND OF THE INVENTION

Improved methodologies for maximizing protein production through recombinant gene expression is an on-going effort in the art. Of particular interest is the development of methodologies that maximize recombinant expression of biologically active proteins for producing commercially useful quantities of these proteins. While prokaryotic, typically bacterial, host cell systems have proven capable of generating large quantities of recombinant proteins, these hosts suffer from a number of disadvantages, including an inability to glycosylate proteins, inefficient cleavage of "pre" or "prepro" sequences from proteins (e.g., inefficient post translational modification), and a general inability to secrete proteins. Consequently the art has sought eukaryotic host systems, typically mammalian host cell systems, for mammalian protein production. One feature of such systems is that the protein produced has a structure most like that of the natural protein species, and, purification often is easier since the protein can be secreted into the culture medium in a biologically active form.

A number of problems still exist however, in mammalian culture systems. Specifically, high levels of production typically are not easily obtained in mammalian systems. In addition, eukaryotic host cells typically have more stringent requirements for culturing and have slower growth rates. Thus, producing large quantities of a recombinant protein requires more than simply culturing a host cell transfected with an expression vector. This is particularly true when the gene of interest encodes a protein that is poorly expressed, e.g., is not produced in abundance and/or is only transiently produced under natural, physiological conditions. Typically, the genes for these proteins have multiple levels of regulation, often at one or more levels of the expression system, e.g., at the level of transcription, translation, post translation modification, secretion and/or activation. Typically these genes, when stably integrated in unamplified, immortalized cells, produce less than about 10–100 ng protein/$10^6$ cells/ml. Maximizing production of these protei'Bns means identifying means for circumventing these levels of regulation.

One approach to achieving enhanced protein production is use of transient cell expression systems wherein cells are transfected with high copy numbers of plasmids that are not expected to integrate in the host cell genome. The plasmids used in transient cell expression systems also can be modified to further enhance their copy numbers during replication post transfection. While the transfection event typically limits the life of these cells to only several generations, reasonable quantities of the desired protein may be produced while the cells remain alive. Because such transient cell systems are short-lived they are not cell systems of choice for commercial production systems. Transient cell systems often are used to screen candidate plasmid or other vector constructions as part of the development of an immortalized, constitutive cell line. But, because transient expression systems are short lived, the long-term productivity of a particular vector construction (or its effect, once integrated, on the viability of a cell after many generations) can not be determined with certainty. Accordingly, a number of plasmid constructions, while productive in transient cell systems, have been determined not to be useful in established cell lines, an event that generally cannot be determined until an established cell line is created.

Two alternative ways primarily focused on by the art for enhancing recombinant gene expression in eukaryotic host systems are enhancing the gene copy number, typically by gene amplification, and enhancing the efficiency of expression of each gene copy. The most common method for enhancing gene copy number is by selecting for gene amplification wherein the host cell is transformed with two genes, linked or unlinked, one of which encodes the desired protein and the other of which encodes an amplifiable selectable marker, such as dihydrofolate reductase (DHFR.) Transformed cells then are cultured in the presence of increasing concentrations of a toxic agent (e.g., methotrexate, where the amplifiable marker is DHFR) whose effects can be nullified by expression of the selectable marker gene. In response to high concentrations of the toxic agent cells survive because they have amplified the copy number of the selectable marker gene and, fortuitously, the desired protein gene. Using this methodology copy numbers in the hundreds and thousands/cell have been achieved.

While gene amplification has proven to be useful, the methodology suffers from several disadvantages pertinent to commercial production. For example, the production of a highly productive cell line by gene amplification alone, e.g., having thousands of copies of the gene of interest, is a time-consuming process often requiring between 6–10 months to complete. Moreover, at very high copy number, verification of the nucleotide sequence integrity for each gene copy in a cell is difficult or not possible. Accordingly, point mutations and other sequence modifications that can alter the biological activity of the protein product may not be detected, and further may pose problems with compliance of government (e.g., FDA) regulations. Moreover, maintenance of such a high copy number requires maintaining the selective pressure by maintaining high levels of the toxic agent in the culture medium. This is both expensive and presents additional regulatory issues when purifying the protein of interest from the culture medium. Finally, and perhaps most importantly, when a gene has multiple levels of expression regulation, merely increasing the copy number of the DNA may not be sufficient to enhance protein production significantly.

One method for enhancing recombinant DNA expression is by means of one or more genes encoding expression effector molecules. Among the effector molecules known in the art are transacting transcription activators which can stimulate transcription of heterologous genes. Examples include the simian virus (SV40) T antigen and adenovirus E1A and E1B proteins which can act on certain viral promoters of heterologous genes, including the cytomegalovirus (CMV) major intermediate early (MIE) promoter. Other molecules reported to have this transctivating activity include the immediate early (IE) proteins of herpes virus, C-myc and genes of the human and simian acquired immunodeficiency virus.

Other viral genes which can effect mammalian protein production are viral translational control effectors. Examples include RNA sequences encoded by the adenovirus, such as the VA genes (VA1 and VA2). Such sequences are believed to assist protein production by assisting with translation initiation, probably by association with one or more translation initiation factors. Other sequences include RNA sequences that can enhance stability of the mRNA transcript.

Cockett et al., ((1990) Nucleic Acids Research 19:319–325 and EP application 378,382) describe the use of the adenovirus E1A genes as an alternative to gene amplification for recombinant protein expression in Chinese hamster ovary (CHO) cells, where the gene of interest is under the CMV promoter control. The level of protein produced is asserted to approach levels achievable by gene amplification, thereby obviating the need for gene amplification. Moreover, the authors see no substantial increase in protein productivity when the E1A gene is introduced to an amplified cell line expressing the gene of interest.

U.S. Pat. No. 5,024,939 describes an unamplified transient cell expression system producing "useful" quantities of a desired gene product in 1 to 14 days without having to establish a continuous production cell system. The authors transfect E1A-expressing cells ("293" cells) with a large number of plasmids carrying the gene of interest under CMV promoter control, and demonstrate increased protein production in these cells for the short lives of the cells. Co-transfection of the 293 cells with the adenovirus VA1 gene appears to double the amount of protein produced in these cells.

It is an object of the instant invention to provide a method for enhancing protein production of poorly expressed genes by recombinant DNA technology. It is another object of the invention to provide immortalized cell lines suitable for commercial exploitation wherein the cells are stably transfected with the gene of interest and are competent to constitutively express the gene of interest, and methods for producing these cell lines. Still another object of the invention is to provide cell lines and methods for creating them, exhibiting high recombinant protein productivity while maintaining a low copy number per cell of the recombinant DNA sequences encoding the protein. Yet another object is to provide cell lines that can be adapted to grow inlow serum or serum-free medium.

Importantly, it is another object of the instant invention to provide means for producing commercially-feasible quantities of morphogenic proteins from cultures of immortalized, stably transfected CHO cell lines.

These and other objects and features of the invention will be apparent from the description, drawings, and claims which follow.

SUMMARY OF THE INVENTION

An improvement in recombinant protein production methodologies now has been discovered which has particular application for the expression of "low expression" or "poorly expressing" genes. As a result of this invention, commercial scale production quantities of hard-to-produce proteins now can be obtained from stably transfected, constitutively expressing eukaryotic cells. Moreover, the cell lines taught by this invention exhibit high recombinant protein productivity while maintaining a low copy number per cell of the recombinant DNA sequences encoding the protein. The cell lines of the invention also can be adapted to grow in low serum or even serum-free medium without significantly compromising cell growth or protein productivity.

The invention involves the multiple transfection of an immortalized eukaryotic cell with a gene of interest and at least one, and preferably, two expression effector genes of viral origin competent to effect expression of the gene of interest, culturing the transfected cell under appropriate selection conditions such that the transfected DNA is stably integrated into the cell genome, and selecting a clone that expresses at least 1 µg protein/$10^6$ cells/ml at post logarithmic phase, for cells grown in a "batch" or "terminal" cell culture. In a preferred embodiment, the clone expresses at least 5 µg protein/$10^6$ cells/ml, or at least 10 µg protein/$10^6$cells/ml. As will be appreciated by those having ordinary skill in the art, higher protein productivity can be obtained by modifying culturing conditions, for example, to enhance cell growth or cell number. In another preferred embodiment, the gene of interest is cotransfected with a means for amplifying the gene, and the cell is cultured under selection conditions that induce gene amplification. While any means for gene amplification is contemplated to be useful, the currently preferred means of gene amplification is by cotransfection of a gene encoding an amplifiable selection marker, such as for example, DHFR or adenosine deaminase, in operational association with a transcription unit. Most preferably, the amplifiable selection marker gene is on the same nucleic acid or vector that carries the gene of interest.

While the method of the invention is described with reference to a single cell, as will be appreciated by those having ordinary skill in the art, this is only for ease of description and the method is most efficiently carried out using a plurality of cells.

As used herein, "vector" is understood to mean any nucleic acid comprising a nucleotide sequence of interest and competent to be incorporated into a host cell and recombining with and integrating into the host cell genome. Such vectors include linear nucleic acids, plasmids, phagemids, cosmids and the like.

As used herein, "gene expression" is understood to refer to the production of the protein product encoded by a DNA sequence of interest, including the transcription of the DNA sequence and translation of the mRNA transcript.

As used herein, "poorly expressed genes" is understood to describe genetic sequences, e.g., DNA sequences that can be acted on by an RNA polymerase to produce an mRNA transcript, and which are not easily expressed and for which only low levels, e.g., less than 10–100 ng protein/$10^6$ cells/ml are produced in an unamplified, stably integrated immortalized eukaryotic host cell system, and for which less than about 100–1000 ng protein/$10^6$/ml are produced in amplified cell. For example, a highly amplified eukaryotic cell is a transfected cell subcloned sufficiently to contain about 1000 or more copies of the gene of interest stably integrated into the host cell's genome and in operative association with a strong promoter/enhancer unit.

Typically, examples of poorly expressed genes are genes whose expression is highly regulated under naturally occurring conditions. Examples of such genes include protein hormones, Factor VIII, TPA (tissue plasminogen activator), and the class of proteins called tissue morphogens or morphogenic proteins(see, for example, PCT/US92/07432 (WO93/05751); or PCT/US93/08808.) Poorly expressed genes are characterized as being highly regulated at one or more levels of expression, e.g., at the level of transcription, translation, post translational modification, secretion and/or protein activation.

Another class of genes for which substantial protein production is difficult to obtain include non-native, biosynthetic or otherwise artificial genes, such as genes created by rational design, and which contain one or more non-native DNA and/or RNA sequences or structures with which the host expression system is unfamiliar and which may limit or otherwise interfere with efficient protein production. An example of such an artificial sequence which does not occur in nature is the single chain binding site molecule (also referred to in the art as "BABS," "biosynthetic antibody binding sites" molecules) wherein a light and heavy chain are encoded in a single DNA sequence, linked by a sequence encoding a polypeptide linker. (see, for example, U.S. Pat. Nos. 5,132,405 and 5,091,513). To date, it is not certain what the limiting step or steps in efficient expression of these genes may be; such limitations may include inefficient secretion.

In a preferred embodiment of the invention the gene of interest encodes a member of the class of proteins called morphogenic proteins as defined in USSN 8/091,395 and in PCT/US92/01968 (WO92/15323) or PCT/US92/07432 (WO93/05751) or PCT/US93/08808, the disclosures of which are incorporated herein by reference. These morphogenic proteins contemplated by the invention include, but are not limited to, the group consisting of OP1, OP2, OP3, BMP2, BMP3, BMP4, BMP5, BMP6, BMP9, DPP, Vgl, Vgr, 60A protein, GDF-1, GDNF, dorsalin-1, and amino acid sequence variants thereof which do not alter substantially the morphogenic activity of these proteins in vivo. As defined in these specifications the members of this class of proteins are characterized as competent for inducing the developmental cascade of cellular and molecular events that culminate in the formation of new organ-specific tissue, including any vascular and connective tissue formation as required by the naturally occurring tissue. Specifically, the morphogens are competent for inducing all of the following biological functions in a morphogenically permissive environment: (1) stimulating proliferation of progenitor cells; (2) stimulating differentiation of progenitor cells; (3) stimulating the proliferation of differentiated cells and (4) supporting the growth and maintenance of differentiated cells. In a particular embodiment, the proteins can induce the full developmental cascade of bone tissue morphogens, including the migration and proliferation of mesenchymal cells, proliferation and differentiation of chondrocytes, cartilage matrix formation and calcification, vascular invasion, osteoblast proliferation, bone formation, bone remodeling, and hematopoietic bone marrow differentiation.

The genetic sequences encoding these proteins and descriptions for their isolation from various genomes are disclosed in the art as follows:OP1 (U.S. Pat. No. 5,011,691; Ozkaynak et al. (1990) EMBO J. 9: 2085–2093 and USSN 07/841,646, filed Feb. 21, 1992, now issued as U.S. Pat. No. 5,266,683 on Nov. 30, 1993, OP2 (Ozkaynak (1992) J. Biol. Chem. 267:25220–25227 and USSN 07/841,646); BMP 2,3,4 (Wozney et al. (1988) Science 242:1528–1534); BMP5,6 (Celeste et al. (1991) PNAS. 87:9843–9847); BMP 9 (WO93/00432, published Jan. 7, 1993); GDF-1 (Lee (1991) PNAS 88:4250–4254); DPP (Padgett et al. (1987) Nature 325:81–84); Vg-1 (Weeks (1987) Cell 51:861–867); Vgr-1 (Lyons et al (1989) PNAS 86:4554–4558); 60A (Wharton et al. (1991) PNAS 88:9214–9218); GDNF (Lin et al. (1993) Science 260: 1130–1132) and Dsl-1 (dorsalin-1, Basler et al. (1993) Cell 73: 687–702), the disclosures of which are incorporated herein by reference.

The genetic sequences encode proteins the immature translation products of which comprise a secretion signal sequence and a "pro" domain, both of which are cleaved to release polypeptide chains of about 135–145 amino acids, depending on the protein species. The members of the class are characterized in part by significant amino acid homology (e.g., at least 70% homology) within the C-terminal 102–106 amino acids, including seven cysteines, substantially conserved in their linear arrangement in the C-terminal sequence.

The proteins typically are secreted as disulfide linked dimers and are rendered soluble under physiological conditions by non-covalent association with one or more copies of the cleaved pro domain. A detailed description of these proteins and their physiological forms is disclosed in USSN 08/040,510, Mar. 31, 1993, the disclosure of which is incorporated herein by reference.

The morphogens are inactive when reduced, but are active as oxidized homodimers and when oxidized in combination with other morphogens of this invention. Thus, as defined herein, a morphogen is a dimeric protein comprising a pair of polypeptide chains, wherein each polypeptide chain comprises at least the C-terminal six cysteine skeleton defined by the C-terminal 96 amino acids of the mature OP1 polypeptide sequence, including functionally equivalent arrangements of these cysteines (e.g., amino acid insertions or deletions which alter the linear arrangement of the cysteines in the sequence but not their relationship in the folded structure), such that, when the polypeptide chains are folded, the dimeric protein species comprising the pair of polypeptide chains has the appropriate three-dimensional structure, including the appropriate intra- or inter-chain disulfide bonds such that the protein is morphogenically competent in vivo.

Particularly useful sequences for use as morphogens include the C-terminal domains of the class morphogenic proteins, e.g., the C-terminal 96–102 amino acid residues of Vgl, Vgr-1, DPP, OP-1, OP-2, BMP-2, BMP-4, GDF-1, GDNF, Dsl-1, 60A protein, BMP3, BMP5 BMP6 and BMP9, all of which include at least the conserved six or seven cysteine skeleton. In addition, biosynthetic constructs designed from the generic sequences, such as COP-1, 3–5, 7, 16, disclosed in U.S. Pat. No. 5,011,691, also are useful. Other sequences include the inhibins/activin proteins (see, for example, U.S. Pat. Nos. 4,968,590 and 5,011,691).

Accordingly, other useful sequences are those sharing at least 70% amino acid sequence homology or "similarity", and preferably 80% homology or similarity with any of the sequences above. These are anticipated to include allelic, species variants and other amino acid sequence variants (e.g., including "muteins" or "mutant proteins"), whether naturally-occurring or biosynthetically produced, as well as novel members of this morphogenic family of proteins. As used herein, "amino acid sequence homology" is understood to mean amino acid sequence similarity, and homologous sequences share identical or similar amino acids, where similar amino acids are conserved amino acids as defined by Dayoff et al., *Atlas of Protein Sequence and Structure; vol.5*, Suppl.3, pp.345–362 (M.O. Dayoff, ed., Nat'l BioMed. Research Fdn., Washington D.C. 1978.) Thus, a candidate sequence sharing 70% amino acid sequence homology with a reference sequence requires that, following alignment of the candidate sequence with the reference sequence, 70% of the amino acids in the candidate sequence are identical to the corresponding amino acid in the reference sequence, or constitute a conserved amino acid change thereto. "Amino acid sequence identity" is understood to require identical amino acids between two aligned sequences. Thus, a candidate sequence sharing 60% amino acid identity with a reference sequence requires that, following alignment of the candidate sequence with the reference sequence, 60% of the amino acids in the candidate sequence are identical to the corresponding amino acid in the reference sequence.

As used herein, all homologies and identities calculated use OP-1 as the reference sequence. Also as used herein, sequences are aligned for homology and identity calculations using the method of Needleman et al. (1970) J. Mol. Biol. 48:443–453 and identities calculated by the Align program (DNAstar, Inc.) In all cases, internal gaps and amino acid insertions in the candidate sequence as aligned are ignored when making the homology/identity calculation.

The currently preferred protein sequences useful as morphogens include, but are not limited to, those having greater than 60% identity, preferably greater than 65% identity, with the amino acid sequence defining the conserved six cysteine skeleton of human OP1 (e.g., the C-terminal 96 amino acids). These most preferred sequences include both allelic and species variants, e.g., naturally-occurring sequence variants, of the OP-1 and OP-2 proteins, including the Drosophila 60A protein.

The expression effector molecules useful in the methods and cell lines of the invention preferably are of viral origin and are competent to stimulate transcription and translation. In one embodiment the expression effector molecules of viral origin are encoded in the bovine papilloma virus early region DNA (See Maat, J. et al (1979) Gene 6:75 et seq. and *Molecular Cloning: A Laboratory Manual*, 2ed. Sambrook et al. eds., Cold Spring Harbor Laboratory Press, N.Y. (1989), Chapter 16, for a description of this region of the virus.)

In another embodiment, the expression effector molecules of viral origin include trans-acting transcription activators ("transcription transactivators") competent to act on and stimulate the promoter that induces transcription of the gene of interest. Typically, these transactivators are of viral origin and can act on their own or on other particular viral promoters. In a preferred embodiment, the transactivating protein is encoded by the adenovirus E1A or E1B gene, the herpesvirus IE gene, C-myc, or the TAT gene of the human immunodeficiency virus (HIV). For example, where the transactivating protein is E1A, the preferred promoters include the constitutive CMV-MIE promoter, and the adenovirus E1A and late region promoters. Where the transactivator is encoded by the TAT gene, a preferred promoter is the HIV-LTR. Other transactivator-promoter combinations are described in the art and are contemplated herein. As described in more detail below, the viral transcription activator gene need not be under the control of a promoter which limits its expression, but such a promoter may be employed.

In another preferred embodiment, the expression effector molecules of vital origin also include RNA sequences operative to promote translation of the transcript encoded by the gene of interest. These sequences may include mRNA stabilizing sequences or segments which act on the translation machinery itself. For example, currently most preferred sequences are those encoded by the adenovirus, most particularly the adenovirus VA genes, including VA1 and VA2. These genes encode RNAs that are though to act, at least in part, by interaction with one or more translation initiation factors. The bovine papilloma virus early region DNA is anticipated to include one or more of these stabilizing sequences.

Preferably, the transfection system comprises both a gene encoding a transcription transactivating sequence and a gene encoding an RNA stabilizing sequence that stimulates translation.

In another preferred embodiment, the transfected cells are subcloned under selective pressure to induce amplification of the gene of interest. The currently preferred method includes the use of a gene encoding an amplifiable selection marker. An example of such a marker gene used with success in the method of the invention includes the DHFR gene, and selection with methotrexate. However, other amplifiable genes are well known in the art and are contemplated herein, including, without limitation, adenosine deaminase and glutamine synthetase. A general description of gene amplification and useful selectable marker genes are described in a number of texts available in the art, including R. E. Kellems, *Gene Amplification in Mammalian Cells*, Marcel Dekker, New York (1993). Where the amplifiable selection gene is not dominant acting, the host cell to be transfected preferably is genotypically deficient in the selection gene.

Host cell lines contemplated to be useful in the method of the invention include any eukaryotic cell lines that can be immortalized, i.e., are viable for multiple passages, (e.g., greater than 50 generations), without significant reduction in growth rate or protein production. Where cell lines are to be used to produce biologicals intended for administration to humans, the host cell preferably is not a human cell. Currently preferred cell lines are those having simple media component requirements, and which can be adapted for suspension culturing. Most preferred are mammalian cell lines that can be adapted to growth in low serum or serum-free medium. Particularly, where the gene of interest encodes a morphogenic protein, the preferred host cell line is a mammalian tissue cell line, e.g., a uro-genital cell line including kidney or bladder cell line, liver, lung, ovary, cardiac muscle, or other smooth muscle cell line, including a smooth muscle cell line of the gastrointestinal tract. Representative cell lines include, but are not limited to, Chinese hamster ovary (CHO); canine kidney (MDCK); or rat bladder (NBT-2), and the like. Useful cell lines can be obtained from the American Type Culture Collection (ATCC), Rockville, Md. or from the European Collection of Animal Cell Cultures, Porton Down, Salsbury SP40JG, U.K.

Where the gene of interest is a "low expression" or "poorly expressed" gene, the currently most preferred methodology includes co-transfection of the gene of interest, the transactivating gene and the RNA stabilizing sequence, and subcloning candidate cells under amplification conditions so as to produce a cell line that produces at least 1 µg protein/$10^6$ cells/ml, more preferably at least 5µg protein/$10^6$ cells/ml, or at least 10µg/$10^6$ cells/ml in a "batch" or "terminal" cell culture where the protein is harvested from the culture medium when the cells are in post-logarithmic phase.

An important feature of the invention is that the method of manufacturing a transfected host cell line provides a low copy number of the gene of interest while still producing high levels of the protein product. This feature endows the invention with regulatory utility by easing the burden of compliance with federal good manufacturing practices. For example, low copy number in the transfected cell line enabled and disclosed herein will permit ease of documentation and standardization of production methodologies pursuant to U.S. Food and Drug Administration rules and regulations.

With respect to the transfection process used in the practice of the invention, all means for introducing nucleic acids into a cell are contemplated including, without limitation, $CaPO_4$ co-precipitation, electroporation, DEAE-dextran mediated uptake, protoplast fusion, microinjection and lipofusion. A key to the invention is the complement of vectors with which the cell is transfected, rather than the mechanical or chemical process by which the DNA incorporation is accomplished.

Moreover, the invention contemplates either simultaneous or sequential transfection of the host cell with vectors containing the DNA sequences to be integrated into the genome. In one preferred embodiment, host cells are simultaneously transfected with at least two unlinked vectors, one of which contains the gene of interest (also referred to as the "reporter gene"), and the other of which contains a gene encoding a transcription transactivator. More preferably, genes encoding an amplifiable selection gene, and a translation stimulating sequence also are cotransfected, either by incorporation of these sequences on one or both of the two unlinked vectors, or by simultaneous transfection with a third vector, followed by early transfectant selection based on cell growth and enhanced protein production. Simultaneous transfection permits for random assortment of the genes to be incorporated into the host cell and allows the cells independently to regulate the copy number and expression level of the transfecter sequence. Thus, the final optimal combination is determined empirically for each cell, in essence by each cell, by selecting for high protein producing cells that are also healthy, stable transfectants. The exact copy number of the gene elements and/or expression control elements for each gene's expression may vary among the clones selected, but all are characterized by producing at lease 1 μg protein per ml per $10^6$ cells at post-logarithmic phase in a terminal cell culture. In a preferred embodiment, the cells also are characterized by having a low copy number of the gene of interest which may be due, at least in part, to the presence of the transcription transactivator.

While there is no reason a priori why all elements cannot be transfected on a single vector, as will be appreciated by those skilled in the art, a single vector limits the possible constellations of the elements on the vector and, therefore, in the cell, rather than allowing for their random assortment in cells. Where all elements, e.g., the gene of interest, the amplifiable marker and the expression effector sequences are transfected on a single vector, the transactivating transcription effector gene preferably is under control of a weakened promoter to limit the expression of this gene sequence.

Alternatively, the DNA sequences can be transfected sequentially. For example, the vector comprising the transcription activator, e.g., E1A, may be transfected first, and its DNA allowed to stably integrate within the host cell genome prior to subsequent transfection with the remaining sequence(s). Also contemplated in the invention is the use of the expression effector genes under weak or strong promoter/enhancer units.

A key to realizing the benefit of the instant invention's enhanced production of poorly expressed genes is culturing the above-described transfected cell lines in low serum or serum-free medium. The currently preferred serum-free medium is a lipid-modified medium wherein the modification comprises a lipid membrane phosphoglyceride ester degradation product. A representative formulation of the preferred serum-free medium is presented in U.S.S.N. 08/124,676 (filed Sep. 22, 1993) and incorporated herein by reference. Other media, including other serum free media, are described in the art.

Thus, in view of this disclosure, skilled genetic engineers can construct transfectants which overcome the production problems associated with certain low expression genes. Specifically, those skilled in recombinant DNA techniques can design appropriate DNA vectors encoding for the protein of interest, an amplifiable marker gene, transcription transactivators, and translation stimulators, and then use the methods of manufacturing transfectants disclosed herein to obtain large quantities of proteins. Such proteins can be in their native forms or truncated analogs, as well as muteins, fusion proteins, or other constructs capable of mimicking the biological activity of the protein of interest in vivo.

BRIEF DESCRIPTION OF THE DRAWINGS

The foregoing and other objects and features of the invention, as well as the invention itself, may be more fully understood from the following description, when read together with the accompanying drawings, in which.

DETAILED DESCRIPTION

A methodology and cell line useful for the large scale production of recombinant mammalian gene expression now has been discovered. The method has particular utility in providing useful quantities of protein encoded by "hard-to-express" genes. The method of the invention can produce stable, immortalized mammalian cell lines that constitutively express a gene of interest to produce a protein at a concentration of at least 1 μg protein/$10^6$ cells/ml without relying on high copy numbers of the gene of interest. Moreover, the method of the invention requires substantially shorter times for producing high expressing, fully amplified cells.

Figure 1:
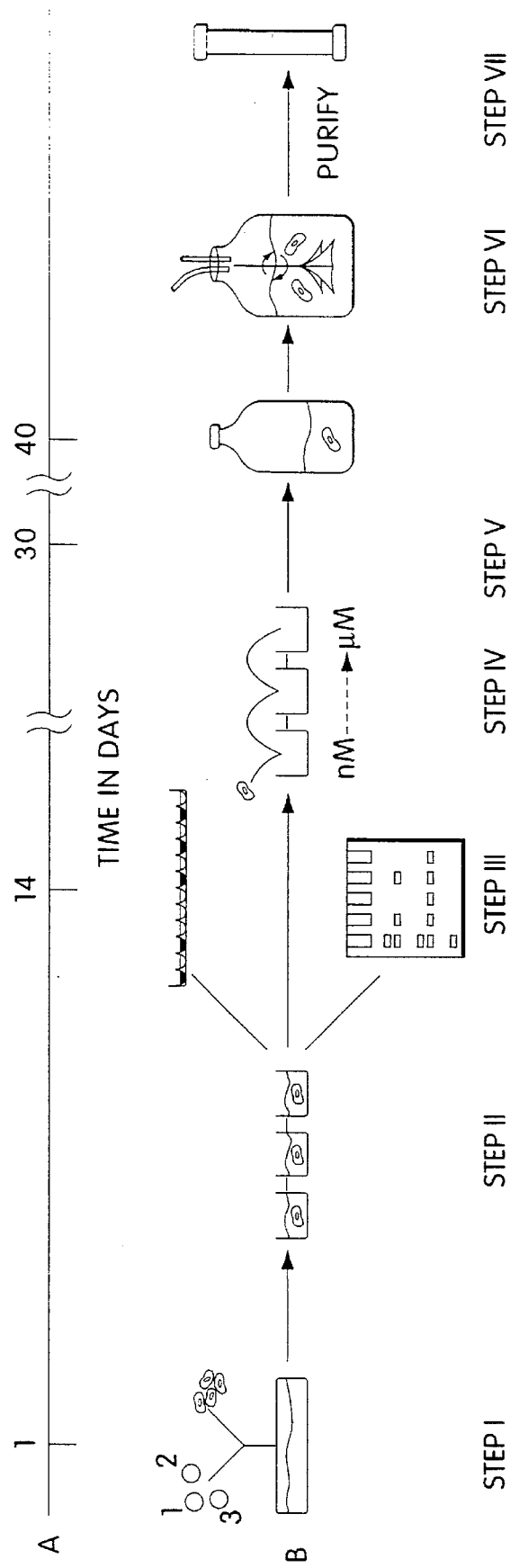
FIG. 1 (A and B) is a schematic representation of a selection protocol of the invention, wherein FIG. 1, panel A depicts a time line corresponding to the protocol depicted in FIG. 1, panel B.

A general selection protocol useful in the method of the invention is depicted in FIG. 1. As can be seen in step I of the protocol, an immortalized eukaryotic host cell, typically a mammalian cell, is transfected with nucleic acids carrying three DNA sequences. The first DNA sequence carries the reporter gene (gene of interest) operatively associated with a transcription promoter/enhancer unit of viral origin. The second DNA carries a viral gene encoding a transactivating protein competent to act on and stimulate transcription from the viral promoter unit that induces transcription of the reporter gene. The third DNA carries a viral gene encoding an RNA stabilizing sequence operative to promote translation of the reporter gene transcript. In FIG. 1, these DNA sequences are carried on separate vectors and the vectors are transfected simultaneously. However, as will be appreciated by those having ordinary skill in the art, the DNA sequences can be transfected sequentially. For example, the cell first can be transfected with one or more nucleic acids carrying the translation promoter sequence and/or the transcription transactivator sequences, and stable integrants obtained, and the cell subsequently transfected with the reporter gene. In addition, two or three DNA sequences can be carried on a single nucleic acid. Where two of the three sequences are carried on a single vector, combinations that may be particularly useful include the viral effector sequences, or the reporter gene and the translation effector sequence. Where all three sequences are carried on a single vector, means for modulating expression of the transcription transactivator may need to be provided. For example, the adenovirus E1A gene generally is believed to interfere with cell growth at high levels of expression. Where the E1A gene is transfected on a separate nucleic acid than that of the reporter genes, for example, the sequences can assort randomly, in a given cell, increasing the possibility of selecting for a clone that produces optimal protein levels of both genes. Because the range of assortment events will be reduced where the genes occur on a single nucleic acid, means for modulating, e.g., limiting the E1A gene expression, for example, by means of a weakened promoter, may be required.

In step II of FIG. 1, transfected cells are replated, e.g., in individual wells and in selective medium, grown to confluency, and the concentration of reporter protein produced (the protein of interest) determined from aliquots of culture medium taken from each well, typically by ELISA or Western blot (step III.) Candidate cells then are cloned/ amplified by multiple passages in a limited dilution series in the presence of increasing concentrations of amplification medium, until high expressing, fully amplified cells are obtained, (step IV of FIG. 1.) Without being limited to a particular theory, transfection with the viral transcription transactivating gene appears to limit the degree of amplification allowed in a cell so maximum amplification clones can be achieved at a faster rate and, in the presence of lower concentrations of toxic agent than in cells amplified in the absence of the viral effector genes. Moreover, the presence of the transcription and translation effector genes work synergistically to increase expression from each gene copy. In the method of the invention, step IV occurs in fewer steps than in cells amplified in the absence of the viral effector genes, (typically requiring only about one month vs six months.) Once clones exhibiting the desired protein production level are obtained (step V), cloned cells can be cultured in a large-scale production protocol (step VI) to produce large (at least 2 liters) quantities of the desired protein, which then can be purified from the culture medium using a standard, desired methodology (step VII).

Following the method outlined herein, stable, high producing clones can be obtained. The combination of viral effector genes has a synergistic effect on protein production, enhancing levels beyond those achievable in the presence of only one of the two effector genes or by gene amplification alone for poorly expressed genes. Moreover, where the reporter gene is a poorly expressed gene capable of producing protein at less than 100–1000 ng/$10^6$ cells/ml in a highly amplified cell line, the method and cell line of the invention which combine the step of cotransfection with viral effectors and the step of amplification of the reporter gene unexpectedly can increase the level of protein produced beyond the level obtained using either step alone.

Provided below are detailed descriptions of the various elements that comprise the methods and compositions of the invention, as well as methods for their application, and numerous, nonlimiting examples which 1) illustrate useful, exemplary vector constructions, transfection protocols, useful cell line sources, and culturing, selection and subcloning protocols; 2) provide assays for testing candidate cell lines for their protein productivity and cell growth capabilities; and 3) provide methods for culturing cells in low serum or serum-free media. Also provided are examples demonstrating the method of the invention with two genes known to be poorly expressed genes: a morphogenic protein representative of the class of tissue morphogens as defined herein (OP-1), and a gene encoding a single chain binding site (a non-native DNA sequence).

I. Useful Cells

Any immortalized eukaryotic cell line suitable for long term culturing conditions is contemplated to be useful in the method and compositions of the invention. Useful cell lines should be easy to transfect, are capable of stably maintaining foreign DNA with an unrearranged sequence, and have the necessary cellular components for efficient transcription, translation, post-translation modification, and secretion of the protein. Where the cell is to be transfected with a non-dominating selection gene, the cell genotype preferably is deficient for the endogenous selection gene. Preferably, the cell line also has simple media composition requirements, rapid generation times, and can be adapted to grow in a suspension culture. Particularly useful cell lines are mammalian cell lines, including myeloma, HeLa, fibroblast, embryonic and various tissue cell lines, e.g., kidney, liver, lung and the like. A large number of cell lines now are available through the American Type Culture Collection (ATCC, Rockville, Md) or through the European Collection of Animal Cell Cultures (ECACC) (Porton Down, Salsbury, SP4OJG, U.K.).

Where the reporter gene encodes a morphogenic protein as defined herein, particularly useful cell lines are envisioned to include mammalian cell lines, including, without limitation, uro-genital cell lines, including kidney and bladder cells, lung, liver, cardiac muscle or other smooth muscle cell lines and other cell lines known to express endogenous genes encoding morphogenic proteins.

II. Useful Promoter Units for Reporter Genes

The reporter gene should be operatively associated with a promoter unit capable of being stimulated by a vital transacting transcription activator as described herein. Useful promoters include the human cytomegalovirus major intermediate-early promoter (hCMV-MIE) or the adenovirus early promoter (E1A, E1B promoter), or the adenovirus late region promoter. Preferably, the CMV-MIE promoter is an intron-free form of the promoter, so-called the CMV-MIE "short" promoter. CMV promoter sequences or plasmids containing them can be purchased commercially, e.g. from Invitrogen, Inc., San Diego (pCDM8) and from Clontech, Inc., Palo Alto. Preferably, the transcription further is stimulated by the inclusion of a cis-acting enhancer sequence, e.g., the mouse mammary tumor virus long terminal repeat (MMTV-LTR) or the Rous sarcoma virus long terminal repeat (RSV-LTR-) Enhancer sequences or plasmids containing them also are commercially available (e.g., from Invitrogen Inc., San Diego, or Clontech Inc., Palo Alto), and/or also are available through the ATCC and ECACC.

III. Useful vital expression effector genes

The vital expression effector genes useful in the methods and cell lines of the invention are competent to act on the promoter that induces transcription of the reporter gene and/or to act on the reporter gene's transcript or the translation machinery.

At least one of the expression effector genes is a viral transacting transcription activator. Useful sequences include those encoded by the adenovirus-2 E1A and E1B genes, as well as by the bovine papilloma virus early region DNA. Details on these sequences and vectors carrying these sequences can be found in Maat, J. et al. (1979) Gene 6:75, and in EP 0378,382 and Cockett, (1990) *Nucleic Acids Research* 19:319–325 all incorporated herein by reference. Whole bovine papilloma DNA virus can be obtained commercially, e.g., from IBI, New Haven (Catalog #33040.)

The authors of EP 0378,382 state that appropriate levels of the transcription activator can be obtained by choice of a suitable promoter/enhancer unit for its transcription (e.g., a weak promoter is preferred and a stable transcription activator expressing cell is produced before transfection with the reporter gene.) Alternatively, and as currently preferred herein, the activator gene is co-transfected together with the reporter gene, and the transfected cells individually allowed to determine the appropriate, combined level of all recombinant, expressed genes, including the optimal level of the activator gene product for that cell when present in the cell in combination with the reporter gene and gene product.

The second viral defector preferably is a translation activator, preferably an RNA sequence competent to enhance translation of the reporter gene. Preferably, the RNA sequence is encoded by an adenovirus VA gene, preferably at least VA1. Other useful sequences include a portion of the bovine papilloma virus early region DNA. Details of these sequences also can be found in Maat, J., et al. (1979) Gene 6:75, EPO 3378, 382 and Cockett et al. (1990) *Nucleic Acids Research* 19: 219–325; in Schneider et al. (1984) Cell 37:291 et. seq. and in Thimmappaya et al. (1982) Cell 31:543–551, the disclosures of which all are incorporated herein by reference. Like the transcription activator sequence, the translation activator sequence may be transfected under control of its own promoter/enhancer unit, or under a stronger or weaker promoter unit. The choice of promoter/enhancer unit is less critical, as high expression clones having the optimal combination of activator and reporter gene sequences will be determined empirically by the screening and selection protocol in the preferred embodiment of the invention.

By screening for good cell growth and selecting for high reporter gene expression, optimal concentrations of all elements for maximal expression of a given reporter gene more easily is obtained than by artificially predetermining the level any one element should have in the cell.

IV. Vector Construction Considerations

Optimal vector design for transfection into eukaryotic cells should include appropriate sequences to promote expression of the gene of interest as described supra, including appropriate transcription initiation, termination, and enhancer sequences, as well as sequences that enhance translation efficiency, such as the Kozak consensus sequence. Preferred DNA vectors also include a marker gene as a means for selecting for the presence of the vector DNA in a cell. The marker gene also may provide means for amplifying the copy number of the gene of interest, and may also include a second gene for resistance to cytotoxins.

Substantial progress in the development of mammalian cell expression systems has been made in the last decade, and many aspects of these systems' features are well characterized. A detailed review of the state of the art of the production of foreign proteins in mammalian cells, including useful cell lines, protein expression-promoting sequences, marker genes, and gene amplification methods, is disclosed in Bendig, Mary M., (1988) *Genetic Engineering* 7:91–127.

V. Transfection Considerations

Any method for incorporating nucleic acids into cells of interest is contemplated in the method of the invention. Calcium phosphate ($CaPO_4$), followed by glycerol shock is a standard means used in the art for introducing vectors, particularly plasmid DNA into mammalian cells. A representative method is disclosed in Cockett et al. (1990) Biotechnology 8: 662–667, incorporated herein by reference. Other methods that may be used include electropotation, protoplast fusion, particularly useful in myeloma transfections, microinjections, lipofections and DEAE-dextran mediated uptake. Methods for these procedures are described in F. M. Ausubel, ed., *Current Protocols in Molecular* John Wiley & Sons, New York (1989).

Generally, plasmids are transfected in equal molar concentrations and cells are plated.at a density of about 1–2 $10^6$ cells/dish. As will be appreciated by those having skill in the art, optimal DNA concentrations per transfection will vary by transfection protocol. For a calcium phosphate transfection, for example, preferably 5–10 µg plasmid DNA per plasmid type is transfected. So, where a simultaneous triple transfection is contemplated, 15–30 µg are transfected in total. In addition, the DNA to be transfected preferably is essentially free of contaminants that may interfere with DNA incorporation. A standard means used in the art for purifying DNA is by ethidium bromide banding.

VI. Amplification Considerations

One of the better characterized methods of gene amplification in mammalian cell systems is the use of the selectable DHFR gene in a dhfr- cell line. Generally, the DHFR gene is provided on the vector carrying the gene of interest, and addition of increasing concentrations of the cytotoxic drug methotrexate leads to amplification of the DHFR gene copy number, as well as that of the associated gene of interest. DHFR as a selectable, amplifiable marker gene in transfected Chinese hamster ovary cell lines (CHO cells) is particularly well characterized in the art. The instant invention may be practiced using this particular amplification marker. Other useful amplifiable marker genes include the adenosine deaminase (ADA) and glutamine synthetase (GS) genes. (See, R. E. Kellems, *Gene Amplification in Mammalian Cells*, Marcel Decker (1992).

VII. Exemplary Large Scale Culture Production Protocols

Any means available or known in the art for large scale eukaryotic cell culturing (e.g., at least 2 liters) is anticipated to be useful for culturing the cell lines taught by this invention. Two general culturing methodologies practiced in the art are the "continuous flow" systems, where cells are exposed to fresh media at regular intervals to replenish any spent nutrients, and the "terminal" or batch culture system, where cells are grown to confluency under a defined set of culture parameters, and the production medium harvested when cells have entered post-logarithmic phase. In addition, cells may be grown as a suspension culture or as attached, monolayers of cells.

The type of culture system used and the media replenishment regimen chosen are determined by the host cell line requirements. For example, some mammalian cell lines are not adaptable to suspension cultures while others are unable to remain securely attached to a substrate. Additionally, some cell lines are highly vulnerable to the shear forces associated with suspension and/or bioreactor culture conditions. In the case of these cell lines, addition of agents such as anti-foam and/or shear-minimizing agents may permit use of suspension cultures. Another factor critical in the choice of culture system is the host cell line's gas requirements, with gas transfer and gas composition being two important considerations for optimal cell growth in vitro. Numerous references are available that describe means for creating large scale culture conditions and general considerations. Exemplary references include R. J. Freshney, *Animal Cell Culture: A Practical Approach* 2d.ed., Oxford University Press, New York, 1992, and M. Butler, *Mammalian Cell Biotechnology: A Practical Approach*, Oxford University Press, New York, 1991.

VIII. Media Considerations

Transfectants obtained with the above-described preferred protocol are initially conditioned in media containing serum proteins. Preferably, under production conditions, the cells are adapted to growth in low serum or serum-free conditions, to limit interference with protein purification. Useful media includes media containing 0.1%–0.5% dialyzed fetal calf serum. In a preferred embodiment, the low serum or serum-free media is supplemented with one or more lipid membrane phosphoglyceride ester degradation products, as disclosed in USSN 08/124,676, filed Sep. 22, 1993 and incorporated herein by reference. Other media components useful in production protocols include protease inhibitors. A representative reference detailing growth supporting media considerations for mammalian cell culture includes *ATCC Media Handbook*, Cote et al., ed., American Type Culture Collection, Rockville, Md. (1984).

As indicated above and as will be appreciated by these having ordinary skill in the art, particular details of the conventional means for transfection, expression, and purification of recombinant proteins are well documented in the art and are understood by those having ordinary skill in the art. The instant invention enables and discloses improvements to these conventional means comprising a combination of transfection vectors which achieves markedly enhanced recombinant expression of low expressing genes including genes encoding morphogenic proteins, using immortalized, eukaryotic cells.

Further details on the various technical aspects of each of the steps used in recombinant production of foreign genes in mammalian cell expression systems can be found in a number of texts and laboratory manuals in the art, such as, for example, F. M. Ausubel et al., ed., *Current Protocols in Molecular Biology*, John Wiley & Sons, New York, (1989.)

EXAMPLE 1 CONSTRUCTION OF REPRESENTATIVE EXPRESSION EFFECTOR VECTORS

Figure 2A:
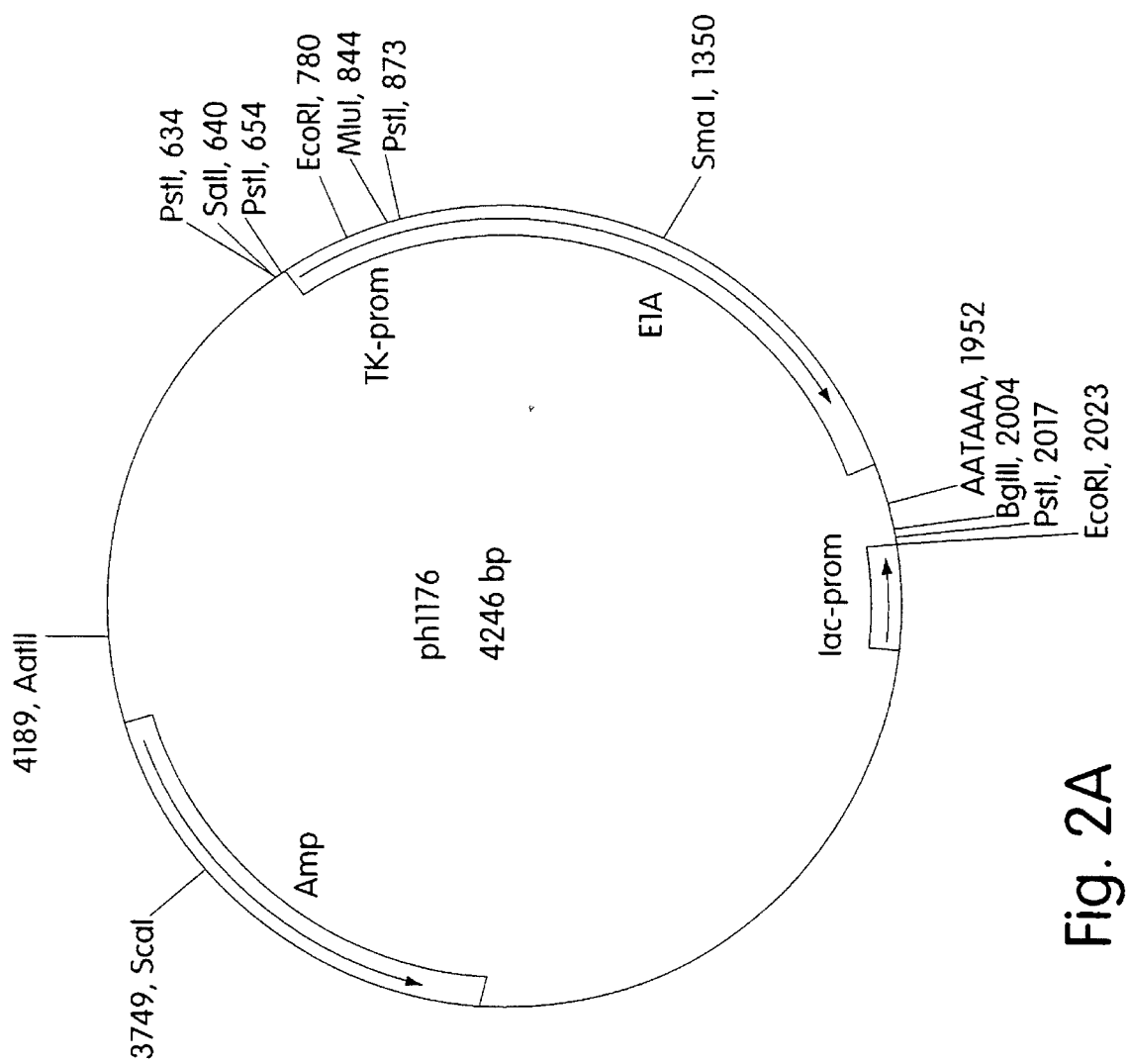
FIGS. 2A, 2B and 2C are restriction maps of three exemplary vectors for transfecting cells with the adenovirus E1A or VA1 genes.

The pH1176 vector (FIG. 2A) employs the adenovirus E1A gene (Seq. ID No. 1) under the control of the thymidine kinase promoter as a transactivating transcription activator. The E1A coding region was isolated by polymerase chain reaction (PCR) with adenovirus DNA as template and priming the reaction with synthetic oligo nucleotide primers to gene terminal sequences on the upper and lower strands (Seq. ID Nos. 2 and 3) with a commercially available thermal cycler and Reagent kit (e.g., GeneAmp, Perkins-Elmer Corp., Norwalk) and following manufacturer's instructions in a standard protocol. (See, for example, Saiki et al. (1985) Science 230:1350–1354.) The fragment was cloned in a standard, commercially available pUC cloning vector e.g., SK-Bluescript, Stratagene, Inc., Palo Alto. The herpes simplex virus thymidine kinase promoter was isolated as a 5' SalI to 3' HindII fragment from another plasmid (pTK-HGH, Allegro Systems, San Juan Capistrano) and fused to a StuI site upstream of the E1A coding region. The fragment bearing the TK-promoter and E1A was cloned in a pUC plasmid resulting in plasmid pH1176 (FIG. 2A). Seq. ID No. 1 describes the nucleotide sequence of the Pst 1—ECORI fragment of pH 1176. Maintenance of low copy number in the transfected cells under selective pressure can be verified to ensure incorporation and maintenance of the E1A gene, e.g., by Southern blot or gel assay wherein the level of detected target DNA is compared to a known quantity.

Figure 2B:
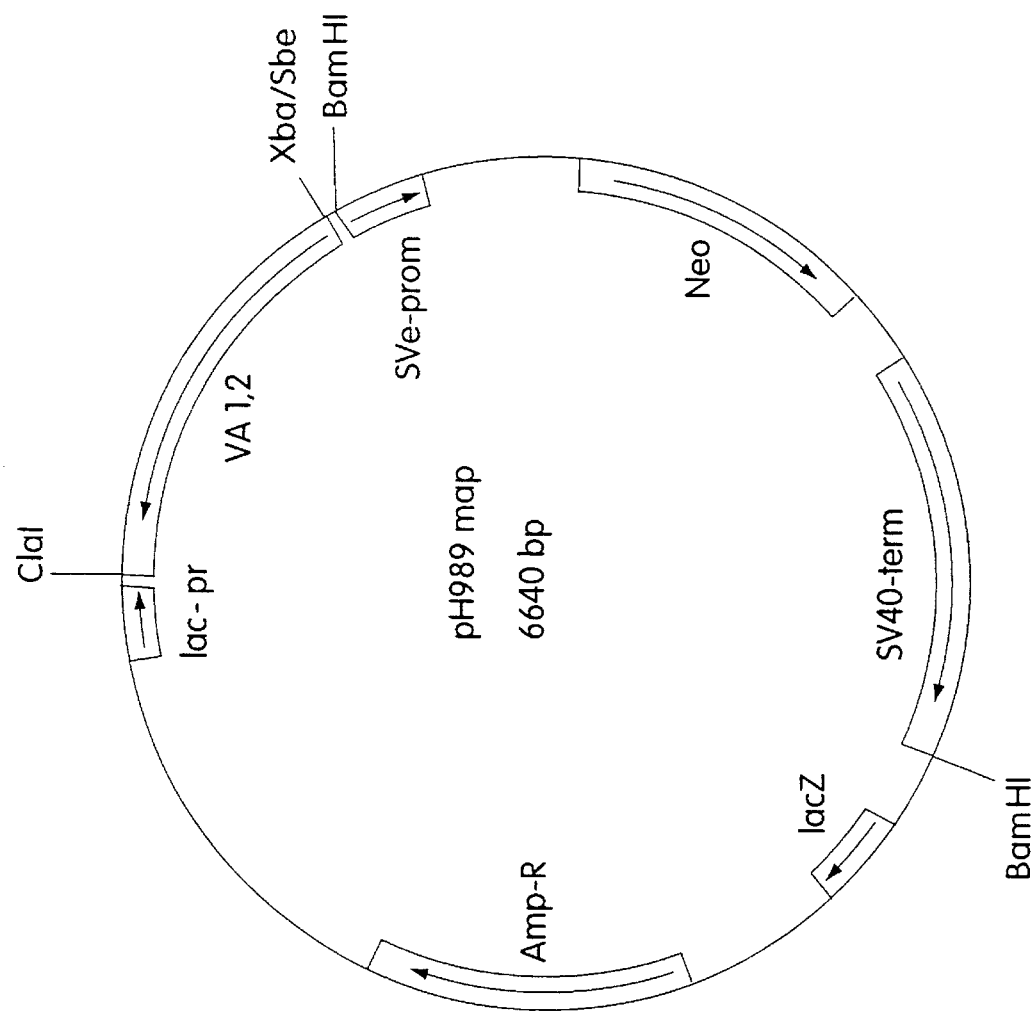
Figure 2C:

The pH989 (FIG. 2B) and pH1130 (FIG. 2C) vectors employ the adenovirus VA1 gene (Seq. ID No. 4) as a translation stimulator (e.g., an RNA sequence competent to promote translation of the transcript encoded by the gene of interest. Cloning of the adenovirus VA1/VA2 gene complex was achieved as follows: the VA1 and VA2 complex was isolated from adenovirus DNA by PCR using two synthetic oligo-nucleotides to gene terminal sequences (upper and lower strands)(Seq. ID Nos. 5 and 6) and standard conditions for PCR. The primers added a new upstream PstI site and a downstream PvuII site. The PstI to PvuII fragment was cloned into the PstI and ECORV sites of the SK(-) Bluescript cloning vector (Stratagene, Inc., Palo Alto, Calif.) resulting in plasmid pJ13: plasmid pJ13 was then incorporated into final vectors pH 989 and pH 1130 as follows.

In the case of pH989, the neo expression element was from the pMamneo expression vector (Clontech, Inc.) was subcloned into the BamHI site of a standard pUC cloning vector, resulting in plasmid pH989. The plasmid orientation (with regard to the BamHI insert) in which the neogene is colinear with the lac promoter of pUC was chosen for the next step, the addition of the VA1 gene. The VA1DNA was excised from pJ13 at flanking poly-linker sites, SpeI and ClaI, and the fragment was inserted between the XbaI and ClaI sites of the plasmid pH988 resulting in pH989.

In the case of pH1130, a modified dhfr gene containing a minimal upstream untranslated region was constructed by site directed mutagenesis and a 5' PvuII site was introduced only a few nucleotides upstream of the ATG initiation condon. At the 3' end a SalI site was added next to a natural BglII site. Seq. ID No. 4 describes the nucleotide sequence of the Pst 12—EcoRI fragment of the pH1130 vector and includes both the VA gene sequence (e.g., nucleotides 1 to 1330) and the DHFR gene sequence.

The tailored dhfr gene was then inserted into plasmid pH989 in place of the neogene. For this purpose pH989 was opened at a unique StuI site, located between the SV40 promoter and the neogene, and at a unique SalI site, downstream or 3' of the neogene and dhfr, as a PvuII to SalI fragment, was inserted. The end of PvuII and StuI sites are compatible for ligation and both sites are lost in the process. The resulting plasmid, pH1130, contains VA1 and dhfr.

EXAMPLE 2 MORPHOGEN DNA VECTORS

FIG. 3 (A–D) discloses restriction maps of various exemplary expression vectors designed for OP1 expression in mammalian cells. Each of these vector constructs employs a full-length hOP1 cDNA sequence originally isolated from a human cDNA library (human OP1 see Ozkaynak et al. (1990) EMBO, incorporated herein above by reference, and subsequently cloned into a conventional pUC vector (pUC-18) using pUC polylinker sequences at the insertion sites. The hOP1 cDNA fragment cloned into each of these constructs is either the intact SmaI-BamHI hOP1 cDNA fragment (nucleotides 26–1385 of Seq. ID No. 1 as disclosed in U.S. Ser. No. 841,646 filed Feb. 21, 1992, now issued as U.S. Pat. No. 5,266,683 on Nov. 30, 1993, or Ozkaynak, (1990) EMBO J. 9:2085–2093 incorporated herein above by reference) or modifications of this fragment where the flanking non-coding 5' and/or 3' sequences have been trimmed back, using standard molecular biology methodology. Each vector also employs an SV40 origin of replication (ori). In addition, the early SV40 promoter is used to drive transcription of marker genes on the vector (e.g., neo and DHFR). It will be appreciated by those skilled in the art that DNA sequences encoding truncated forms of morphogenic protein also may be used, provided that the expression vector or host cell then provides the sequences necessary to direct processing and secretion of the expressed protein.

The pH717 expression vector (FIG. 3A) contains the neomycin (neo) gene as a selection marker. This marker gene is well characterized in the art and is available commercially. Alternatively, other selectable markers may be used. The particular vector used to provide the neogene DNA fragment for pH717 may be obtained from Clontech, Inc., Palo Alto, Calif. (pMAM-neo-blue). This vector also may be used as the backbone. In pH717, hOP1DNA transcription is driven by the CMV promoter, boosted by the RSV-LTR and MMTV-LTR (mouse mammary tumor virus) enhancer sequences. These sequences are known in the art, and are available commercially. For example, vectors containing the CMV promoter sequence may be obtained from Invitrogen Inc., San Diego, Calif., (e.g., pCDM8).

Figure 3A:
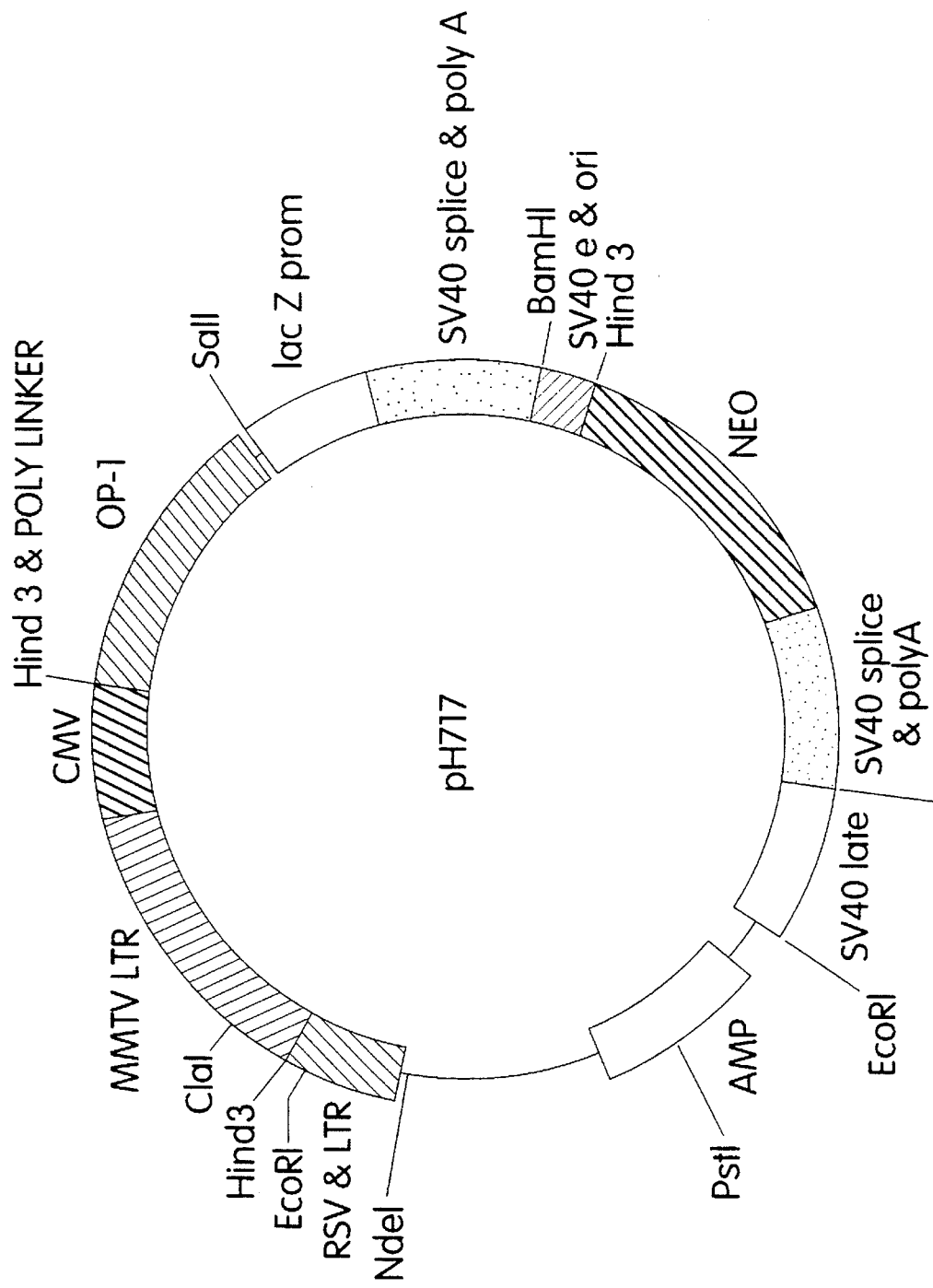
FIGS. 3A, 3B, 3C and 3D are restriction maps of exemplary vectors carrying OP-1 as the reporter gene under control of CMV-MIE constitutive "short" promoter.
Figure 3B:
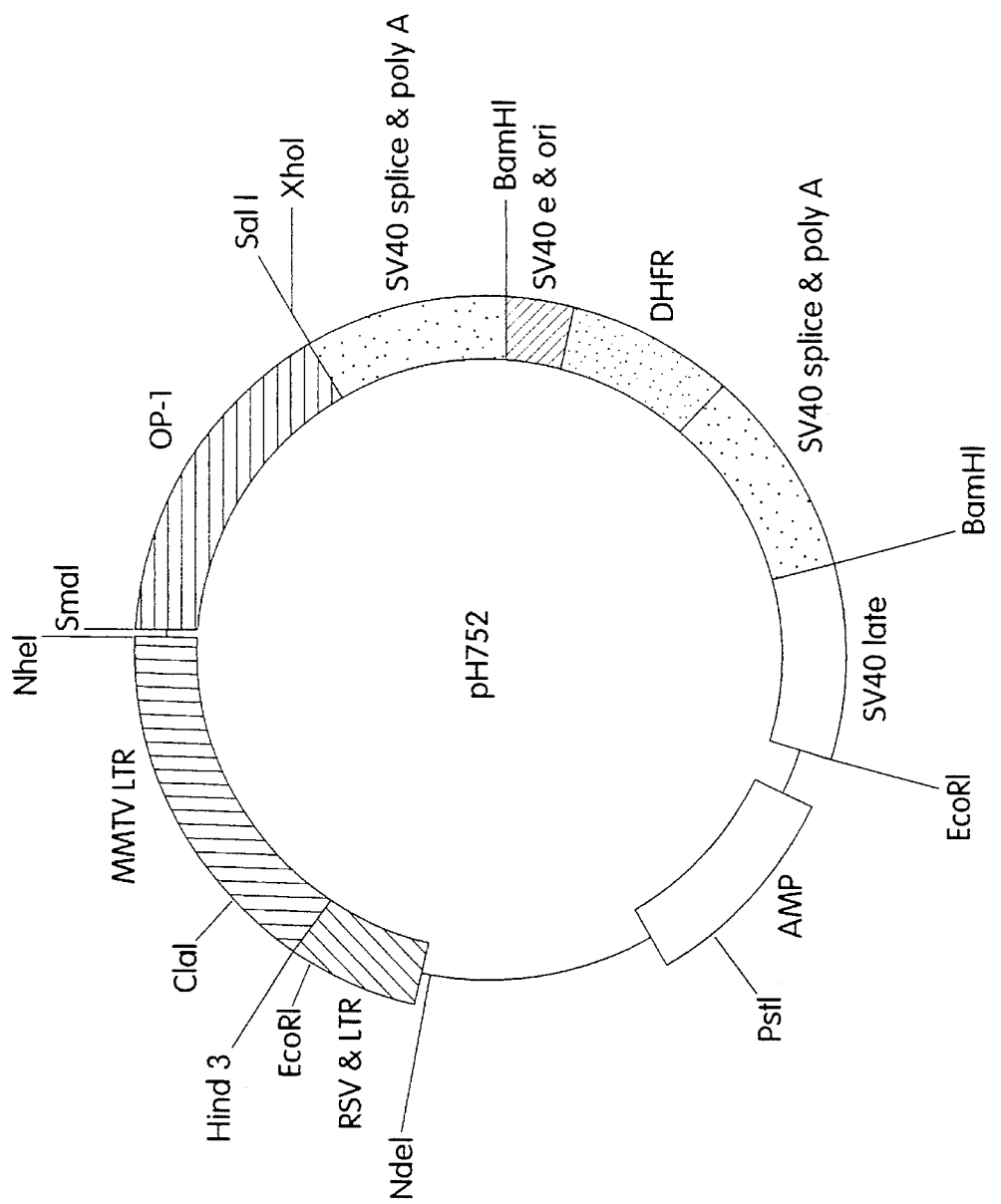
Figure 3C:
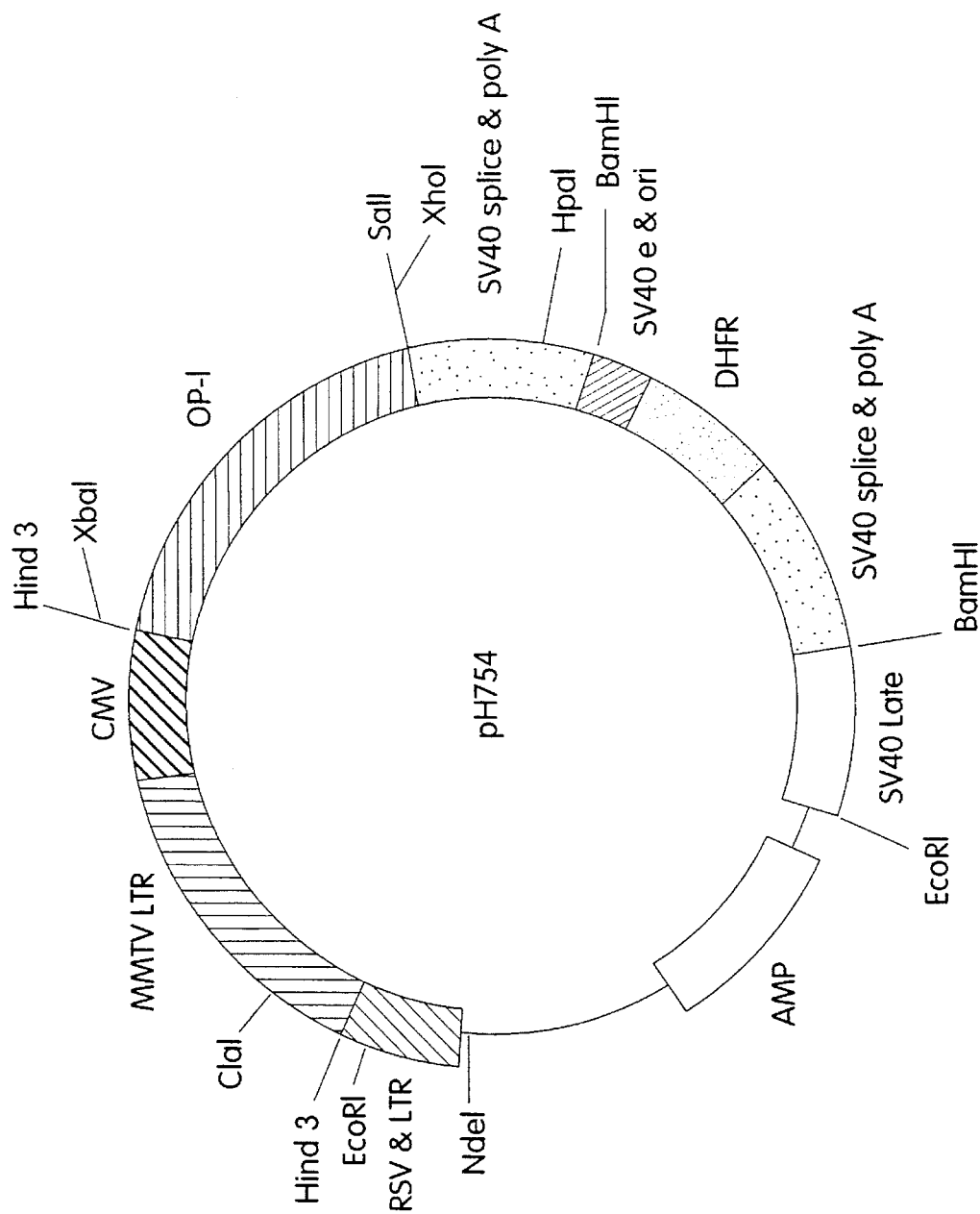
Figure 3D:
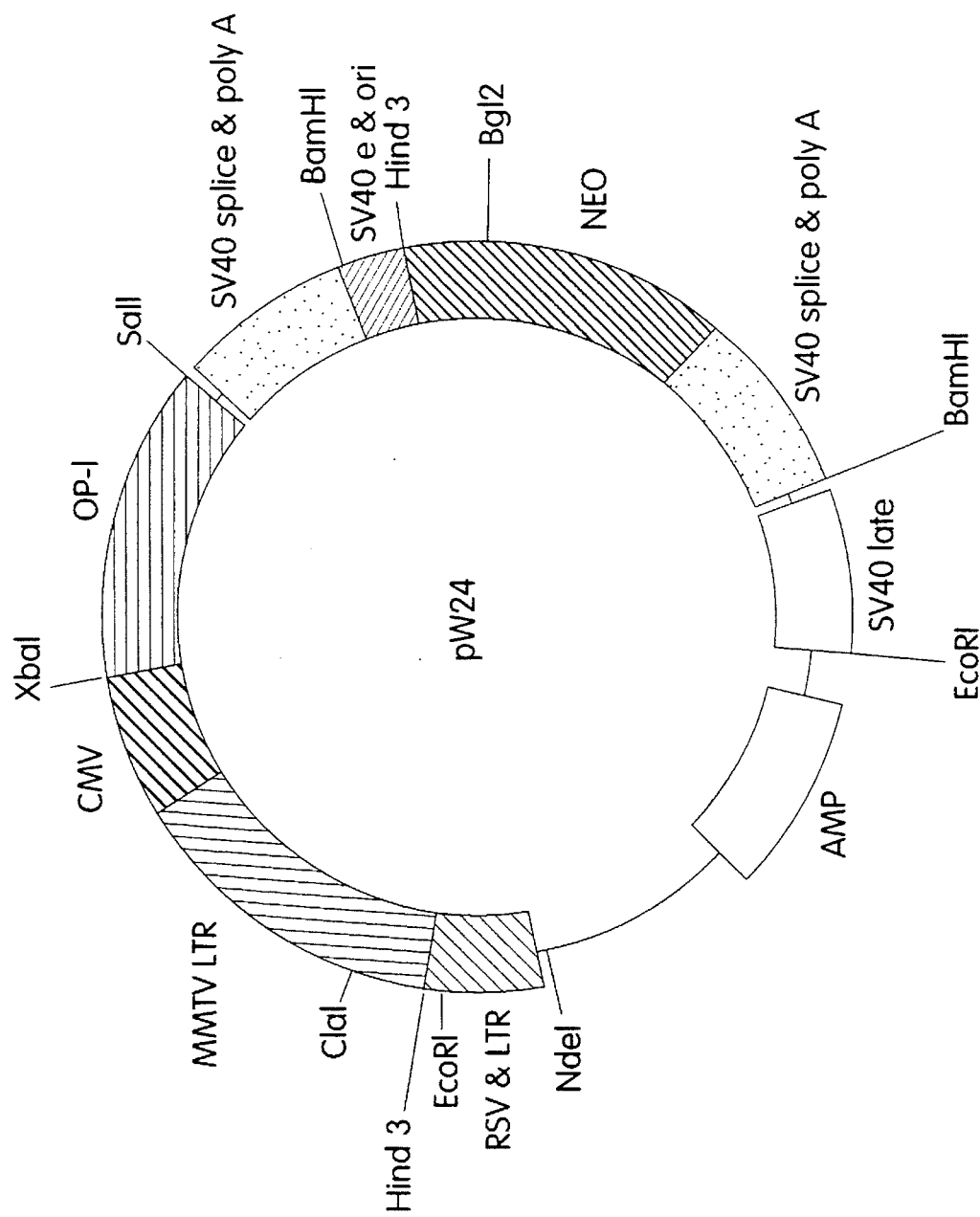

The pH752 and pH754 expression vectors contain the DHFR gene, under SV40 early promoter control, as both a selection marker and as an inducible gene amplifier. The DNA sequence for DHFR is well characterized in the art, and is available commercially. For example, pH754 may be generated from pMAM-neo (Clontech, Inc., Palo Alto, Calif.) by replacing the neogene (BamHI digest) with an SphI-BamHI, or a PvuII-BamHI fragment from pSV5-DHFR (ATCC #37148), which contains the DHFR gene under SV40 early promoter control. A BamHI site can be engineered at the SphI or PvuII site using standard techniques (e.g., by linker insertion or site-directed mutagenesis) to allow insertion of the fragment into the vector backbone. hOP1DNA can be inserted into the polylinker site downstream of the MMTV-LTR sequence (mouse mammary tumor virus LTR), yielding pH752 (FIG. 3B). The CMV promoter sequence then may be inserted into pH752 (e.g., from pCDM8, Invitrogen,Inc.), yielding pH754 (FIG. 3C.) The SV40 early promoter, which drives DHFR expression, is modified in these vectors to reduce the level of DHFR mRNA produced. Specifically, the enhancer sequences and part of the promoter sequence have been deleted, leaving only about 200 bases of the promoter sequence upstream of the DHFR gene.

The pW24 vector (FIG. 3D), is essentially identical in sequence to p754, except that neo is used as the marker gene (see pH717), in place of DHFR.

The pW24 plasmid contains OP-1 cDNA under transcriptional control of the CMV (cytomegalovirus) immediate early promoter. This promoter is derived from pCDM8 and is much shorter than the CMV promoter used by other practitioners. The latter one contains introns and also additional upstream sequences. The selective marker on pW24 is the neogene which supplies resistance to the cytostatic drug G418. In addition the plasmid contains the LTR from rous sarcoma virus and from mouse mammary tumor virus and the SV40 origin of replication. The latter viral enhancer elements (LTR and SV40 ori) are not essential even though they may have some beneficial effects on expression.

Plasmid pW24 was constructed by a 3-part assembly essentially as follows: The pMam-neo vector (Clontech Inc., Palo Alto, Calif.) was opened in its poly-linker/cloning site by restriction digest with NheI and SalI. The CMV promoter from pCDM8 and the human OP-1 gene was then inserted on a SpeI to SalI fragment. During this ligation the NheI and SpeI sites which have compatible ends were both lost.

Prior to this, the CMV promoter had been joined with the OP-1 cDNA, by fusion of the 3' XbaI site flanking the CMV promoter with a 5' NheI site placed upstream of the OP-1 cDNA, in an earlier step. During this ligation the XbaI site and NheI site which have compatible ends were also both lost. The NheI site, flanking OP-1 cDNA was acquired previously when OP-1 cDNA, on a fragment spanning from its natural 5' SmaI site, approximately 20 nucleotides upstream of the ATG, up to the natural BamHI site, approximately 40 nucleotides downstream of the stop codon, with a SalI site attached immediately next to it and was inserted into the pMAMneo vector between the SmaI and SalI sites of its poly-linker insertion site.

EXAMPLE 3 TRANSFECTIONS

In all examples, transfections were by calcium phosphate coprecipitation, performed using standard procedures. CHO cells, from Dr. Lawrence Chasin, Columbia University, N.Y., were cultured in αMEM, containing 5% or 10% fetal bovine serum (FBS), non-essential amino acids, glutamine and antibiotics: penicillin and streptomycin, all being obtained from GIBCO, New York. CHO cells transfected with vectors containing a neogene were cultured in the same growth medium containing the toxin G418 (0.4 mg/ml). CHO cells transfected with vectors containing the DHFR selectable amplifiable gene, were cultured in α-MEM (cuMEM lacking thymidine, glycine and hypoxanthine), 10% dialyzed FBS, and methotrexate (MTX) at 0.02–0.1 μM.

Stable cell line trans#ections were carried out by seeding $1-2 \times 10^6$ cells in a 9 cm. petri dish. Following up to 24-hour incubation in growth medium, each petri dish was transfected with 10–30μg total vector DNA in equimolar amounts, by calcium phosphate coprecipitation followed by glycerol shock using standard methodology. Cells are incubated at 37° C. in growth medium for 24 hours, then transferred to selection medium. All cultures were fed once or twice weekly with fresh selective medium. After 10–21 days, resistant colonies were picked and assayed for protein production.

Table I summarizes the actual experimental transfections performed to determine the effect of the above-described vectors (alone and in combination) on OP1 production. The vectors and the combinations presented in Table I were selected, in part, to determine the optimal configuration of OP1, VA1, and E1A vectors, and in part to determine whether the E1A and/or VA1 genes are crucial for optimal OP1 expression. In Table I, transfections number 1, 2 and 3 are considered "double" transfections since two different genes (not necessarily vectors) have been introduced to the CHO host cell; similarly, transfections number 4 and 5 are considered "triple" transfections since three different genes (not necessarily vectors) have been introduced. "Single" transfections refer to CHO cells transfected only with an OP1-encoding vector.

TABLE I

| TRANS-FECTION | PLASMID (element present/selection marker) |
| --- | --- |
| 1 | pH754 (OP-1/DHFR) + pH989(VA1/neo) |
| 2 | pW24 (OP-1/neo) + pH1130(VA1/DHFR) |
| 3 | pH754 (OP-1/DHFR) + pH1176(E1A/none) |
| 4 | pW24 (OP-1/neo) + pH1130(VA1/DHFR) + pH1176(E1A/none) |
| 5 | pH754 (OP-1/DHFR) + pH989(VA1/neo) + pH1176(E1A/none) |

EXAMPLE 4 SELECTION SCREENING FOR CANDIDATE CELL LINES

Following transfection and growth in selection medium, cells were screened for candidates to be subcloned, essentially as described in FIG. 1.

Using the transfection schemes summarized in Table I above, approximately 30 individual clones from each transfection in Table I were selected, transferred to a 24-well petri dish, and allowed to grow to confluence in serum-containing media. The conditioned media from all surviving clones was screened for protein production using a standard ELISA (enzyme-linked immunosorbent assay) or Western blot. The methodologies for these assay protocols as well as for generating antibodies for use in these assays are well described in the art (see, e.g., Ausubel, and USSN 08/040, 510, filed Mar. 31, 1993 and incorporated herein by reference). A summary of this primary ELISA screening data for OP1 is found in Table II.

TABLE II

OP-1 PRODUCTION BY CHO TRANSFECTANTS

| RELATIVE PROTEIN PRODUCTION | TRANSFECTION NUMBER (from TABLE I) (number clones/category) | | | | |
|---|---|---|---|---|---|
| | 1(VA1) | 2(VA1) | 3(E1A) | 4(VA1, E1A) | 5(VA1, E1A) |
| − | 24 | 24 | 13 | 8 | 13 |
| ± | 1 | 4 | 1 | 5 | 0 |
| + | 2 | 2 | 0 | 3 | 6 |
| ++ | 0 | 0 | 0 | 9 | 8 |
| +++ | 0 | 0 | 1 | 5 | 9 |
| Total Screened: | 27 | 30 | 15 | 30 | 36 |

The data in Table II suggest that the VA1 and E1A genes act synergistically to enhance OP1 expression in unamplified transfected CHO cells. Transfectants resulting from transfection number 1, 2, or 3 produce negligible amounts of OP1, while transfection number 4 and 5 resulted in approximately 57% and 64%, respectively, of the transfectants producing elevated levels of OP1.

EXAMPLE 5 AMPLIFICATION SUB-CLONING / CLONING METHODS DS

Candidate cell lines identified by the screening protocol of Example 4, then were seeded on ten 100 mm petri dishes at a cell density of either 50 or 100 cells per plate, and with a higher MTX concentration (e.g., 1.0–5μm).

After 10–21 days of growth, clones are isolated using cloning cylinders and standard procedures, and cultured in 24-well plates. Clones then are screened for OP1 expression by Western immunoblots using standard procedures, and OP1 expression levels compared to parental lines. Candidate cells showing higher protein production than cells of parental lines then are replated and grown in the presence of a still higher MTX concentration (e.g., 5–20 μm). Generally, no more than 2–3 rounds of these "amplification" cloning steps are necessary to achieve cell lines with high protein productivity. Useful high producing cell lines may be further subcloned to improve cell line homogeneity and product stability.

EXAMPLE 6. CHARACTERIZATION OF TRANSFECTED CLONE a) Copy Number

Southern blots, using standard metehodology, may be used to assess the state of integrated sequences and the extent of their copy number amplification in the host genome. Copy number experiments on various transfections indicates that the triple transfectants, fully amplified, have on the order of 10 copies of the reporter gene, double transfectants of the reporter gene with VA1 have a somewhat higher copy number, (on the order of 100 copies/cell), both of which are significantly smaller than the copy number for single transfectants, fully amplified. (See Table III, below).

b) mRNA Measurements

Transcription levels of transfected OP1 sequences can be measured in the different expression systems by analyzing mRNA levels (Northern blots), using total cellular RNA and conventional hybridization methodology. Northern blots on various transfections indicate that OP1 transcript production is enhanced in double transfectants of OP1/VA1 as compared with single transfectants, more enhanced in double transfectants of OP1/E1A, and still more enhanced in triple transfectants.

c) Protein Measurements

Protein levels may be measured by Western blots (immunoblots) using rabbit antisera against the protein product of interest. Western blot methodologies are well known to those skilled in the art, and may be performed using commercially-available reagents, USSN 08/040,510, incorporated herein above by reference, describes methods for obtaining OP1 antisera and antibodies, as well as various immunoassays. The protein data presented in Table III is for a "terminal" or "batch" culture where protein is harvested when cells have reached post-logarithmic phase.

Interestingly, protein production in the triple transfectant is synergistically enhanced as compared with either single or double transfectants, even though the copy number is significantly lower in these cells and transcript levels are only moderately enhanced.

TABLE III

OP1 PRODUCTION BY CHO TRANSFECTANTS

| TRANSFECTION CATEGORY | PLASMID | OP1(μg/$10^6$ cell/ml) | Copy Number/Cell |
|---|---|---|---|
| Single | pH754(OP1) | ≦1 | 1000 |
| Double | pW24/pH1130(OP1/VA1) | ≦1–2 | 100 |
| Triple | pW24/pH1176/pH1130(OP1/E1A/VA1) | ≧5–10 | 10 |

These data demonstrate that the invention's combination of transfecting DNA sequences markedly enhances production of OP1. As set forth in Table III, triple transfectants produce levels of OP1 which are substantially greater than those produced by single transfectants using significantly fewer copies of the gene, while both categories of double transfectants produce approximately intermediate levels of the OP1 produced by triple transfectants. On the basis of these data, it appears that the transcription activator E1A and the translation enhancer VA1 act synergistically resulting in high expression of the OP1 gene.

EXAMPLE 7 PROTEIN PRODUCTION IN LARGE SCALE PROTOCOLS

A currently preferred method of large scale protein production e.g., at least 2 liters, is by suspension culturing of the host CHO cells. Chinese hamster ovary cells prefer attachment but can be adapted to grow in suspension mode of cultivation. The cells were trypsinized from the dish, introduced to growth media containing 10% FBS and using a pipet, completely suspended to ideally achieve a single cell suspension. This was introduced to a spinner flask and placed in a 37° C. 95% air/5% $CO_2$ humidified incubator. Over a period of time the cells were subcultured in medium with descending concentrations of serum. Within the spinner flasks there is a balance between sufficient agitation rate to maintain a single cell suspension and the shear force associated with the agitation impeller. Due to the nature of 95%air/5% $CO_2$ incubators there is a balance between oxygen absorption/$CO_2$ desorbtion in the medium and agitation rate, as well as, surface to volume ratios.

For example, the production of CHO conditioned medium in suspension cultures was carried out as follows: The adapted cells were introduced into a 3L spinner flask at an initial viable cell density of approximately $2 \times 10^5$ cells/ml. The culture medium was DMEM/F-12 (1:1) (GIBCO, New York) supplemented with 2% FBS. The agitation was approximately 50–60 rpm with a paddle impeller. The culture volume was 1500 mls (half max.) in order to increase relative surface to volume ratio. After 7 days the culture media is harvested, centrifuged at 1500 rpm and the clarified conditioned media stored at 4°.

EXAMPLE 8. CHARACTERIZATION OF OP1 EXPRESSED BY PREFERRED CLONES

Standard biochemical procedures, including apparent molecular weight determined by gel electrophoresis, and/or N-terminal and C-terminal sequencing (by CNBr analysis) can be used to verify the form and structure of the protein produced. Using these methodologies (described in numerous texts available in the art and, for example, in USSN 841,646) the OP1 protein was found to be of the same form as in cells of single transfectants, e.g., mature, full length form (139 amino acids) as well as various N terminally truncated forms, which are characteristic of expression in CHO cells. (See USSN 841,646).

Moreover, using a standard bioassay methodology for verifying the biological activity of osteogenic (morphogenic proteins), e.g., rat ectopic bone formation assay (see U.S. Pat. No. 5,011,691) the biological activity of the protein produced by the method of the invention was determined to be substantially the same half maximum specific activity as that of the protein produced by single transfectants (see, for example, USSN 07/841,646.) Moreover, in all cases successful implants exhibit a controlled progression through the states of matrix-induced endochondral bone development including: transient infiltration by polymorphonuclear leukocytes on day one; mesenchymal cell migration and proliferation on days two and three; chondrocyte appearance on days five and six; cartilage matrix formation on day seven; cartilage calcification on day eight; vascular invasion, appearance of osteoblasts, and formation of new bone on days nine and ten; appearance of osteoblastic and bone remodeling and dissolution of the implanted matrix on days twelve to eighteen; and, hematopoietic bone marrow differentiation in the ossicle on day twenty-one.

EXAMPLE 9 GENERAL ISOLATION/PURIFICATION SCHEME FOR MORPHOGENS

A representative purification scheme for purifying the recombinant morphogenic proteins that is rapid and highly effective is described in USSN 841,646 and is provided below. The protocol described below involves three chromatographic steps (S-Sepharose, phenyl-Sepharose and C-18 HPLC), and produces OP1 of about 90% purity. The purification protocol of choice will vary with the gene to be expressed.

An alternative protocol that also produces protein of high purity is a variant three step chromatography protocol utilizing Zn/IMAC (metal affinity chelating chromatography), hydrophobic interaction chromatography (e.g., phenyl-Toyopearl) and reverse phase (C-18) chromatography. Still other useful related chromatography methods include heparin-Sepharose used in combination with the S-Sepharose column.

For a typical 2L preparation of transfected CHO cells conditioned in 0.5% FCS, the amount of OP1 in the media, estimated by Western blot, is about 10–20mg/L.

Briefly, OP1-containing culture media is diluted to 6M urea, 0.05M NaCl, 13 mM HEPES, pH 7.0 and loaded onto an S-Sepharose column, which acts as a strong cation exchanger. OP1 binds to the column in low salt, and serum proteins are removed. The column is subsequently developed with two step salt elutions. The first elution (0.1M NaCl) removes contaminants and approximately 10% of the bound OP1. The remaining 90% of OP1 then is eluted in 6M urea, 0.3M NaCl, 20 mM HEPES, pH 7.0.

Ammonium sulfate is added to the 0.3 M NaCl fraction to obtain final solution conditions of 6M urea, 1M $(NH_4)_2SO_4$, 0.3M NaCl, 20 mM HEPES, pH 7.0. The sample then is loaded onto a phenyl-Sepharose column (hydrophobic interaction chromatography). OP1 binds phenyl-Sepharose in the presence of high concentrations of a weak chaotropic salt (e.g., 1M $(NH_4)_2SO_4$). Once OP1 is bound, the column is developed with two step elutions using decreasing concentrations of ammonium sulfate. The first elution (containing 0.6M $(NH_4)_2SO_4$) primarily removes contaminants. The bound OP1 then is eluted with a 6M urea, 0.3M NaCl, 20mM HEPES, pH 7.0 buffer containing no ammonium sulfate.

The OP1 eluted from the phenyl-Sepharose column is dialyzed against water, followed by 30% acetonitrile (0.1% TFA), and then applied to a C-18 reverse phase HPLC column. Gel separation of oxidized and reduced OP1 samples show that the reduced and oxidized subunits appear to be identical to that of the naturally-sourced OP purified from bone.

An alternative chromatography protocol (also disclosed in USSN 07/841,646 filed Feb. 21, 1992, now issued as U.S. Pat. No. 5,266,683 on Nov. 30, 1993, and herein incorporated by reference) is to perform the S-Sepharose chromatography in the absence of 6M urea. The bound proteins then are eluted with salt step elutions (e.g., 100–400 mM NaCl). Most of the OP1 is eluted with about 300 mM NaCl. Additional OP1 then can be eluted with 300 mM NaCl in the presence of 6M urea. The 6M urea elution also may be used in place of the non-urea elution to achieve maximum recovery in one step. In addition, OP1 may be eluted from the phenyl-Sepharose column in 38% ethanol-0.01% TFA, thereby eliminating the need to dialyze the eluent before applying it to the C-18 column. Finally, multiple C-18 columns may be used (e.g., three), to further enhance purification and concentration of the protein.

OP1 also will bind hydroxyapatite efficiently, but only in the absence of 6 M urea and at low phosphate concentrations (less than 5 mM phosphate). Bound OP1 can be removed from the column with a step elution of 1 mM to 0.5M phosphate (in 0.5M NaCl, 50 mM Tris, pH 7.0). OP1 elutes at about 250 mM phosphate. Additionally, urea (6M) may be added during the elution step.

EXAMPLE 10 BPV EARLY REGION DNA CO-TRANSFECTION

Figure 4:
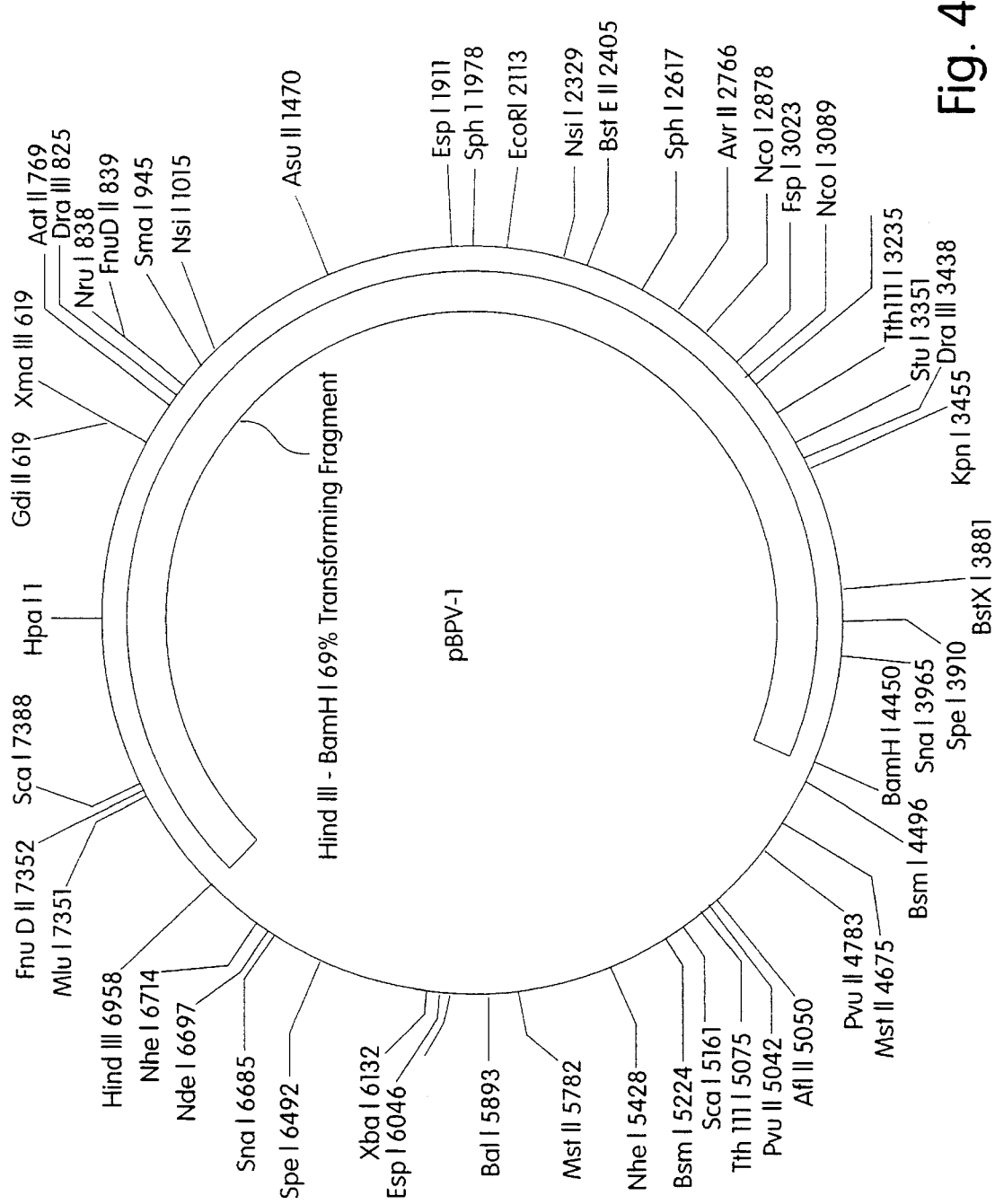
FIG. 4 is a restriction map of an exemplary vector carrying the papilloma virus early region DNA.

Using the transfection and screening protocols described in FIG. 1 and Examples 3 and 4, the effect of bovine papilloma virus early DNA on recombinant OP-1 DNA expression was tested. Here, a vector carrying BPV early region DNA (BPV-1/pML2d vector, FIG. 4, purchased from IBI, New Haven) was transfected into a stable, unamplified OP-1 producing cell line, where the OP-1 gene was present at low copy number (on the order of 1–10 copies.) Alternatively, an E1A-producing vector (e.g., pH1176) was transfected into the same OP1-producing cell line. Candidates screened after the initial transfection demonstrated a 5–8 fold increase in the "double" transfectant (BPV/OP1), over the level of protein produced by the cell alone (OP1) and a 10 fold increase in the alternate "double" transfectant (E1A/OP1), as compared to the cell alone (OP1). Still higher comparative protein levels are anticipated to be detected when the candidate cells are subjected to amplification, cloning and subcloning protocols as described in Examples 5 and 6, to produce clones capable of producing the reporter gene at levels of at least 1, and preferably at least 5 µg protein/$10^6$ cells/ml, where protein is harvested from the medium in a batch culture when cells are in post-logarithmic phase. It is also anticipated that triple transfectants will further enhance protein production. A possible advantage of using BPV over a transactivating sequence like E1A, is in possible secondary effects on growth rates or media requirements conferred on the host cell.

Example 11. Recombinant Single Chain Fv

Figure 5:
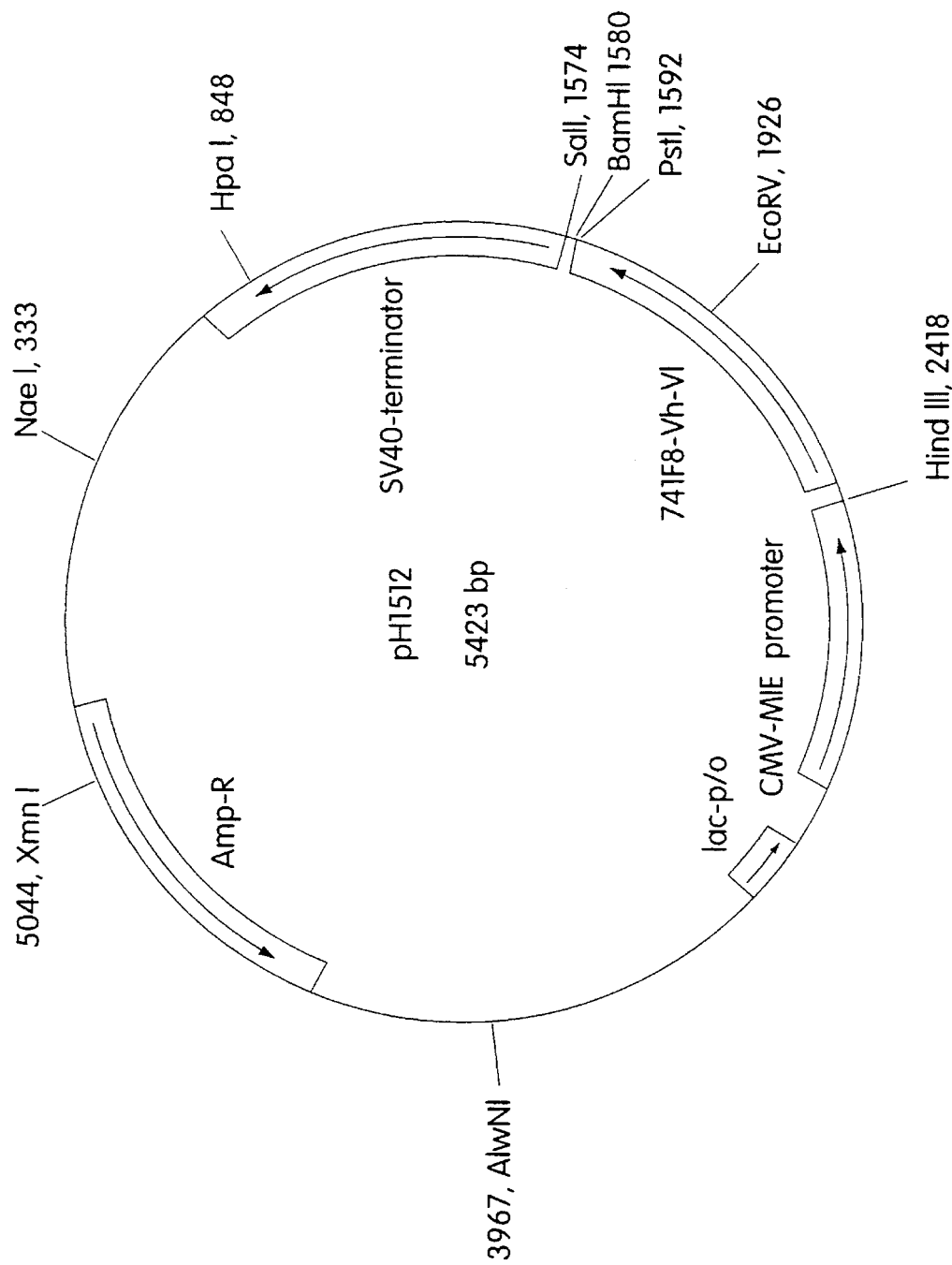
FIG. 5 is a restriction map of an exemplary vector carrying a nucleotide sequence encoding a single chain binding site as the reporter gene under control of the CMV-MIE constitutive "short" promoter.

Using the protocols described in FIG. 1 and Examples 3–5, the method and constructs of the invention were tested on two different artificial genetic sequences encoding single chain Fvs, ("sFv"). These proteins also are referred to in the art as biosynthetic antibody binding site molecules ("BABS"). The two constructs, 741F8 and MOPC315, are well described in the art and in U.S. patent application (Atty. Docket No. CRP-093 filed on even date herewith, the disclosure of which is incorporated herein by reference. The 741F8 construct interacts specifically with the c-erb2 antigen, a known marker associated with breast cancer. MOPC315 recognizes dinitrophenol. An exemplary plasmid, pH1512, carrying the 741F8 sequence under control of the CMV-MIE "short" promoter, and containing a secretion signal sequence obtained from the heavy chain of the 520C9 monoclonal antibody DNA sequence, is presented in FIG. 5. The MOPC315 DNA sequence used also was under control of the CMV-MIE promoter and had its own (native) secretion signal sequence.

Following the protocols described in Examples 3–5, triple transfections of CHO cells were performed with an E1A-containing plasmid (e.g., pH1176), a VA1-containing plasmid (pH1130), and either the MOPC315 or the 741F8 vector. In all cases, high production clones produced at least between 1–6 µg protein per $10^6$ cells/ml in batch cultures, where protein was harvested from the medium when cells were in post-logarithmic phase.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method of producing a morphogen, said method comprising the steps of:
   (a) culturing an immortalized eukaryotic cell comprising transfected DNA sequences operatively integrated into its genome, said transfected DNA sequences encoding
      (i) a viral transcription promoter operatively associated with a DNA sequence encoding a morphogen, said viral transcription promoter being stimulated by a viral transcription activator protein which acts on and induces transcription of said DNA sequence encoding said morphogen to produce an RNA transcript, said transcript, when translated, producing a biologically active morphogenic protein;
      (ii) a transcription activator protein that acts on and stimulates said transcription promoter, wherein the transfected DNA sequence encoding said viral transcription activator protein is operatively associated with, and under the control of a DNA sequence defining a transcription promoter sequence which induces transcription of said vital transcription activator protein DNA sequence, said transcription promoter DNA sequence not requiring limitation of transcription; and,
      (iii) an RNA sequence operative to promote translation of said RNA transcript, under conditions sufficient to produce a population of said cells expressing at least 1 μg morphogen per $10^6$ cell per ml; and
   (b) isolating the morphogen produced by said cells.

2. The method of claim 1, wherein said step of culturing said cell comprises the step of growing said cell in a serum-free medium comprising a lipid membrane phosphoglyceride ester degradation product.

3. The method of claim 1 wherein the copy number of said DNA sequence encoding said morphogen and integrated into the genome of said cell is less than 20 copies per cell.

4. The method of claim 1 wherein the copy number of said DNA sequence encoding said morphogen is less than 10 copies per cell.

5. The method of claim 1 wherein the copy number of said DNA sequence encoding said morphogen is less than 5 copies per cell.

6. The method of claim 1 wherein said vital transcription promoter is selected from the group consisting of promoters derived from adenovirus, rous sarcoma virus, and cytomegalovirus.

7. The method of claim 1 wherein said vital transcription promoter comprises the constitutive major intermediate early promoter of cytomegalovirus.

8. The method of claim 1 wherein said transcription activator protein is a viral transactivating protein which acts on and stimulates transcription of a non-homologous gene.

9. The method of claim 1 wherein said transcription activator protein is the adenovirus E1A protein.

10. The method of claim 1 wherein said DNA sequence encoding said viral transcription activator protein is operatively associated with a DNA sequence defining a transcription promoter sequence which acts on and induces transcription of said transcription activator DNA sequence, said transcription promoter DNA sequence being selected to limit transcription of said viral transcription activator DNA sequence.

11. The method of claim 1 wherein said RNA sequence is a transactivating RNA sequence of viral origin which acts on and enhances translation of an RNA transcript encoded by a non-homologous gene.

12. The method of claim 1 wherein said RNA sequence is VA1.

13. The method of claim 1 wherein said cell produces at least 5 μg morphogen per $10^6$ cell per ml culture medium.

14. The method of claim 1 wherein said cell produces at least 10 big morphogen per $10^6$ cell per ml culture medium.

15. The method of claim 1 wherein said morphogen is isolated when said cell is in post-logarithmic phase.

16. The method of claim 1 wherein said morphogen is a protein selected from the group consisting of: OP1, OP2, OP3, BMP2, BMP3, BMP4, BMP5, BMP6, BMP9, DPP, Vgl, Vgr, 60A protein, GDF-1, Dsl-1, GDNF, and amino acid sequence variants thereof.

17. The method of claim 1 wherein said morphogen is a protein selected from the group consisting of OP 1, OP2, OP3, BMP2, BMP4, BMP5, BMP6, BMP9, and amino acid sequence variants thereof.

18. The method of claim 1 wherein said morphogen comprises an amino acid sequence having at least 70% homology within the C-terminal region, said region consisting of the 102 to the 106 C-terminal amino acids, including the conserved seven cysteine domain, of human OP1.

19. The method of claim 1 wherein said DNA sequence encoding said morphogen encodes OP1 or an amino acid variant thereof.

20. The method of claim 1 comprising DNA sequences encoding at least two morphogens, each said DNA sequence encoding a morphogen being operatively associated with said viral transcription promoter.

21. The method of claim 20 wherein said DNA sequences are independently selected from the group of DNA sequences encoding OP1, OP2, OP3, BMP2, BMP4, BMP5, BMP6, BMP9, and amino acid sequence variants thereof.

22. The method of claim 1 wherein said cell is a mammalian cell.

23. The method of claim 22 wherein said mammalian cell is a kidney, bladder, liver, lung, cardiac muscle, or smooth muscle cell.

24. The method of claim 22 wherein said mammalian cell is selected from the group consisting of Chinese hamster ovary cells, canine kidney cells, and rat bladder cells.

25. The method of claim 22 wherein said mammalian cell is a Chinese hamster ovary cell.

26. The method of claim 1 further comprising means for amplifying the copy number of said DNA sequence encoding said morphogen.

27. The method of claim 26 wherein said amplification means comprises a DNA sequence encoding dihydrofolate reductase (DHFR) in operative association with a promoter sequence that acts on and induces transcription of said DHFR DNA.

28. The method of claim 1 wherein said DNA sequence encoding said RNA sequence comprises part of a nucleic acid separate and independent of a nucleic acid comprising said DNA sequence defining said viral promoter operatively associated with said DNA sequence encoding said morphogen.

29. The method of claim 1 wherein said nucleic acids comprise independent vectors.

30. The method of claim 1 wherein said DNA sequences encoding said transcription activator protein and said RNA sequence occur on a single nucleic acid.

\* \* \* \* \*

UNITED STATES PATENT AND TRADEMARK OFFICE
CERTIFICATE OF CORRECTION

PATENT NO. : 5,614,385
DATED : March 25, 1997
INVENTOR(S) : Oppermann et al.

It is certified that error appears in the above-indentified patent and that said Letters Patent is hereby corrected as shown below:

In claim 14, at column 30, line 60, delete "least 10 big" and insert -- least 10 ug --.

Signed and Sealed this

Seventeenth Day of June, 1997

Attest:

BRUCE LEHMAN

*Attesting Officer*   *Commissioner of Patents and Trademarks*